(12) United States Patent
Naylor et al.

(10) Patent No.: US 8,126,114 B2
(45) Date of Patent: Feb. 28, 2012

(54) SEVEN OR MORE DEGREES OF FREEDOM ROBOTIC MANIPULATOR HAVING AT LEAST ONE REDUNDANT JOINT

(75) Inventors: Michael P. Naylor, Sunnyvale, CA (US); Sohail Sayeh, San Ramon, CA (US)

(73) Assignee: Accuray Incorporated, Sunnyvale, CA (US)

( * ) Notice: Subject to any disclaimer, the term of this patent is extended or adjusted under 35 U.S.C. 154(b) by 473 days.

(21) Appl. No.: 12/251,409

(22) Filed: Oct. 14, 2008

(65) Prior Publication Data

US 2010/0069920 A1    Mar. 18, 2010

Related U.S. Application Data

(60) Provisional application No. 61/096,728, filed on Sep. 12, 2008.

(51) Int. Cl.
*A61N 5/10* (2006.01)
*A61B 19/00* (2006.01)

(52) U.S. Cl. .......................................... 378/65; 606/130

(58) Field of Classification Search .................... 378/17, 378/20, 68, 145, 177, 193–197, 208; 606/130; 600/427, 101; 318/568.11, 568.12
See application file for complete search history.

(56) References Cited

U.S. PATENT DOCUMENTS

| 5,737,500 | A | 4/1998 | Seraji et al. |
| 6,785,572 | B2 * | 8/2004 | Yanof et al. ................... 600/427 |
| 7,447,537 | B1 * | 11/2008 | Funda et al. ................... 600/424 |
| 7,453,227 | B2 * | 11/2008 | Prisco et al. ............. 318/568.11 |
| 7,713,263 | B2 * | 5/2010 | Niemeyer .......................... 606/1 |
| 2005/0234327 | A1 | 10/2005 | Saracen et al. |

FOREIGN PATENT DOCUMENTS

WO    WO 9942259 A1    8/1999

OTHER PUBLICATIONS

PCT International Search Report and Written Opinion of the International Searching Authority, PCT/US09/53560 filed Aug. 12, 2009, mailed Sep. 25, 2009.

* cited by examiner

*Primary Examiner* — Irakli Kiknadze
(74) *Attorney, Agent, or Firm* — Lowenstein Sandler PC

(57) ABSTRACT

A robotic treatment delivery system including a linear accelerator (LINAC), and a robotic manipulator coupled to the LINAC. The robotic manipulator is configured to move the LINAC along seven or more degrees of freedom, at least one of the seven degrees of freedom being a redundant degree of freedom.

32 Claims, 10 Drawing Sheets

```
┌─────────────────────────────────────────────┐
│   providing a medical tool coupled to a robotic │
│ manipulator having seven or more degrees of freedom │
│                    (DOF)                    │
│                     601                     │
└─────────────────────────────────────────────┘
                      │
                      ▼
┌─────────────────────────────────────────────┐
│   moving the medical tool along seven or more DOF │
│         using the robotic manipulator       │
│                     602                     │
└─────────────────────────────────────────────┘
```

FIG. 6

```
┌─────────────────────────────────────────────┐
│  positioning a medical tool to a fixed position using a │
│             robotic manipulator             │
│                     701                     │
└─────────────────────────────────────────────┘
                      │
                      ▼
┌─────────────────────────────────────────────┐
│  maintaining the medical tool at the fixed position, │
│        while moving the robotic manipulator │
│                     702                     │
└─────────────────────────────────────────────┘
```

FIG. 7
SEVEN OR MORE DEGREES OF FREEDOM ROBOTIC MANIPULATOR HAVING AT LEAST ONE REDUNDANT JOINT

RELATED APPLICATIONS

This application claims the benefit of U.S. Provisional Application No. 61/096,728, filed Sep. 12, 2008, the entire contents of which are hereby incorporated by reference herein.

TECHNICAL FIELD

Embodiments of the present invention pertain to the field of robotic manipulators used in medical applications.

BACKGROUND

Conventional robots are designed to do exactly the same thing over and over again, such as in an assembly line for assembly. These robots are programmed and configured to repeat a given motion to perform a specific function. Robots are often implemented to perform a lot of functions, more efficiently, and often more precisely than humans.

Conventional robots, typically, include one or two robotic arm. These robotic arms can have multiple segments that help facilitate movement in differing degrees of freedom (DOF). Some conventional robots employ a computer to control the segments of the robotic arm by activating rotation of individual step motors connected to corresponding segments. Other designs may use hydraulics or pneumatics to actuate movement in the arm segments. Computers allow precise, repeatable movements of the robotic arm.

Prior Selectively Compliant Articulated Robot Arm (SCARA) robots operate with 4 or fewer degrees of freedom ("DOF"). In other words, these robotic arms are designed to move along 4 or fewer axes. A typical application for a conventional robotic arm is that of pick-and-place type machine. Pick-and-place type machines are used for automation assembly, automation placing, printed circuit board manufacturing, integrated circuit pick and placing, and other automation jobs that contain small items, such as machining, measuring, testing, and welding. These robotic arms include an end-effector, also known as robotic peripheral, robotic accessory, robot or robotic tool, end-of-arm (EOA) tooling, or end-of-arm device. The end-effector may be an implement such as a robotic gripper, press tool, paint gun, blowtorch, deburring tool, arc welding gun, drills, etc. These end-effectors are typically placed at the end of the robotic arm and are used for uses as described above. One common end-effector is a simplified version of the hand, which can grasp and carry different objects. Such end effectors typically support maximum payloads ranging from 3 kg-20 kg (6.61-44.09 pounds).

Another type of robot that has been implemented in positioning of a radiation source of a radiation treatment system includes an articulated robotic arm for positioning a radiation source, such as a linear accelerator (LINAC), mounted at a distal end of the articulated robotic arm, for selectively emitting radiation, such as described in U.S. Pat. No. 5,207,223 to Adler.

BRIEF DESCRIPTION OF THE DRAWINGS

Embodiments of the present invention are illustrated by way of example, and not by way of limitation, in the figures of the accompanying drawings and in which:

FIG. 6 illustrates one embodiment of a method for positioning a medical tool using a robotic manipulator.

FIG. 7 illustrates another embodiment of a method for maintaining a medical tool at the fixed position.

DETAILED DESCRIPTION

Figure 1:
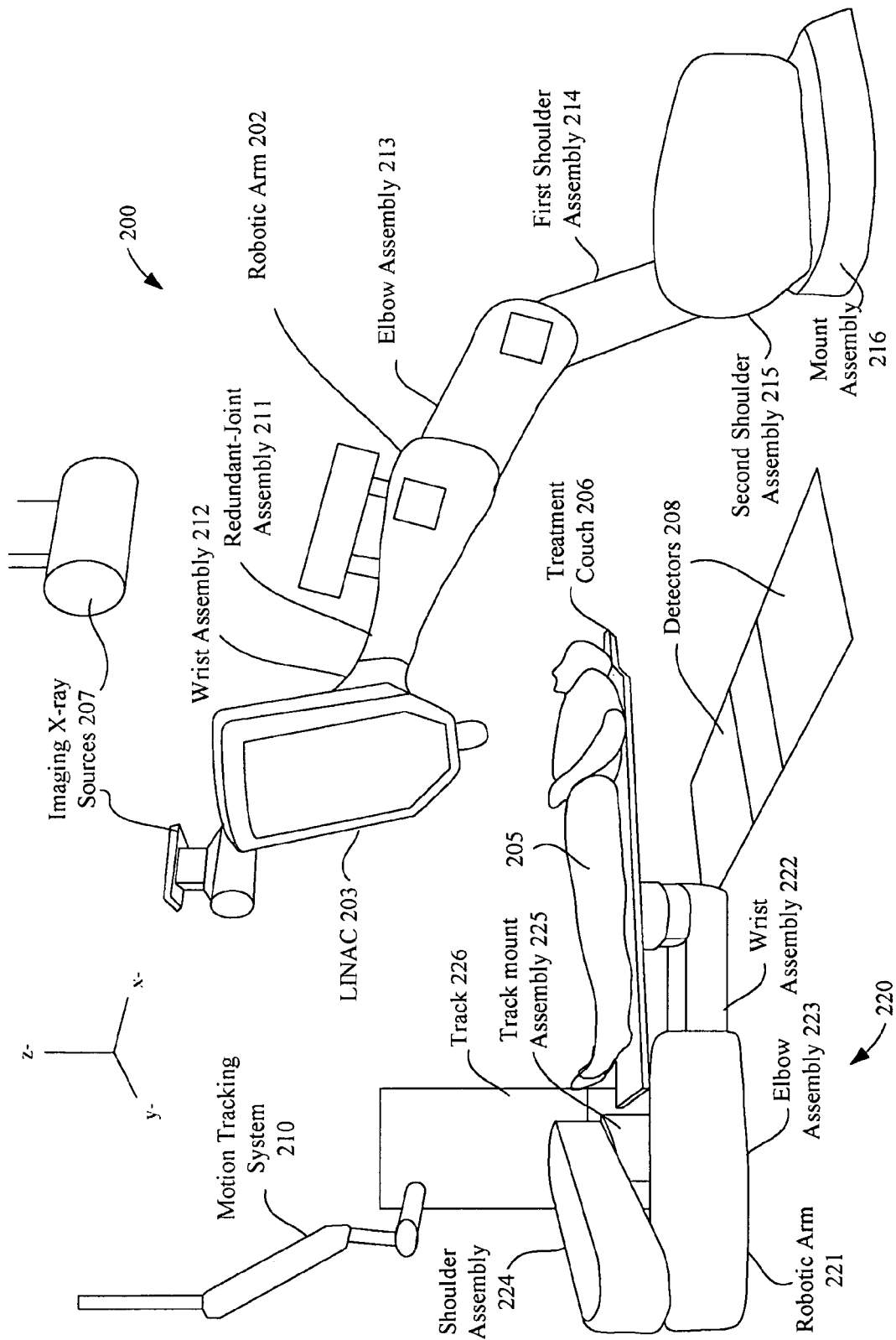
FIG. 1 illustrates one embodiment of a robotic treatment delivery system including a robotic arm having seven degrees of freedom.

Described herein is an apparatus having a medical tool coupled to a robotic manipulator that can move the medical tool along seven or more degrees of freedom, the robotic manipulator having at least one redundant joint. In the following description, numerous specific details are set forth such as examples of specific components, devices, methods, etc., in order to provide a thorough understanding of the present embodiments. It will be apparent, however, to one skilled in the art that these specific details need not be employed to practice the present embodiments. In other instances, well-known materials or methods have not been described in detail in order to avoid unnecessarily obscuring the present embodiments.

The robotic manipulator can position a medical tool attached to the robotic manipulator in seven or more DOF. The robotic manipulator includes multiple rigid links, interconnected by joints, to move the medical tool to move the medical tool in the seven or more DOF. One of the rigid links includes an additional joint (also referred to herein as redundant joint). The multiple rigid links, interconnected by joints, allows either rotational or translational displacement of the medical tool. In one embodiment, the seven DOF includes at least one redundant DOF. The additional joint may be used to move the medical tool in one redundant DOF. For example, multiple rigid links, interconnected by joints, may be used to move the medical tool in six DOF, and an additional joint may be used to move the medical tool in the seventh DOF, the seventh DOF being a redundant DOF. Alternatively, the multiple rigid links, interconnected by joints, may be used to move the medical tool in more than seven DOF, where two additional joints of one of the rigid links are used to move the medical tool in two redundant DOF.

The robotic manipulator may be used in a robotic treatment delivery system for adjusting a position and orientation of a radiation source during, for example, therapeutic radiation treatment. The robotic treatment delivery system includes the robotic manipulator, such as an articulated robotic arm, to position and orient the radiation source, such as a LINAC, in a three-dimensional (3D) space. However, unlike the conventional robotic treatment delivery system, the robotic manipulator of the embodiments described herein includes one or more additional joints than used in the conventional robotic arm having six DOF to move the medical tool along the seventh or more DOF. For example, by adding an additional joint on the link between the third axis (A3) and the wrist assembly, the robotic manipulator can position the joints such that a greater range of motion is capable without putting the patient or treatment couch in danger of collision with the robotic manipulator, as compared to the conventional robotic arm. A similar result may be achieved by adding a third joint at the location of the first and second axes (A1 and A2) to allow the robotic manipulator to rotate the bulk of the robotic manipulator, for example, towards the floor. Using this example, the robotic manipulator can position the medial tool at multiple heights, for example, the robotic manipulator may position a LINAC to a low position for high isocenters, or to a high position for low isocenters.

Since the embodiments described herein include one or more redundant DOF of the seven or more degrees of freedom, the embodiments described herein possess more capabilities than the conventional six DOF robotic arms. While the workspace of the robotic manipulator increases substantially given the extra degrees of freedom, the robotic manipulator having one or more redundant DOF provide an infinite number of configurations for a given tool pose of the medical tool. The workspace is representative of the operating envelop of the robotic manipulator. The one or more redundant DOF of the robotic manipulator may also allow the robotic manipulator to move while the tool position remains constant, as well as enable smooth planar motions. These additional DOF may also allow motions necessary for robust obstacle avoidance. The embodiments described herein may provide more nodes and more paths to get to the nodes (e.g., existing nodes and new nodes). The embodiments described herein may also provide optimization of paths to get to nodes. For example, the embodiments described herein may reduce the time to traverse the nodes, as well as increase the distance margin or clearance between possible obstructions. The embodiments described herein may also be used to position the medical tool at a fixed point using a robotic manipulator, and maintain the medical tool at the fixed point, while moving the robotic manipulator. The embodiments described herein may also be used to maneuver the medical tool through a constrained volume (e.g., obstacle maze) without colliding with an object outside of the constrained volume.

It should be noted in conventional systems, a robotic arm having greater than six DOF has usually been avoided due to the increase complexity of hardware and an increase in required kinematic analysis. However, the embodiments described herein may be used to avoid obstacles and the robotic manipulator may be broken down into two segments, a wrist assembly, and an arm assembly to simplify the kinematic analysis of the tool position and tool orientation. For example, different methods may be used to solve the kinematics of each segment.

It should also be noted that the embodiments described herein have been depicted and described as robotic arms coupled to a LINAC, however, in other embodiments, other robotic manipulators and/or other medical tools may be used. For example, the medical tool may be an imaging source of an imager, a surgical tool, an implantation tool, a treatment couch, or the like.

FIG. 1 illustrates one embodiment of a robotic treatment delivery system 200 including a robotic arm 202 having seven degrees of freedom. The robotic treatment delivery system 200 includes a LINAC 203, and the robotic arm 202 having a wrist assembly 212 and an arm assembly. The wrist assembly 212 is configured to move the LINAC 203 in three rotational DOF (Axes 5-7), and the arm assembly is configured move the LINAC 203 in four DOF (Axes 1-4), one being a redundant DOF. The arm assembly includes multiple rigid links, interconnected by joints, to move the LINAC 203 in the four DOF, including the redundant DOF.

The LINAC 203 is used to produce a beam of radiation that can be directed to a target. The robotic arm may be a highly articulated robotic arm that may have multiple rotational DOF in order to properly position and orient the LINAC 203 to irradiate a target such as a pathological anatomy with a beam delivered from many angles in an operating volume around the patient 205. It should be noted that patient 205 may be a human patient, and alternatively, an animal patient. Also, in other embodiments, other objects than a human or animal may be used. The treatment implemented with the robotic treatment delivery system 200 may involve beam paths with a single isocenter (point of convergence), multiple isocenters, or without any specific isocenters (i.e., the beams need only intersect with the pathological target volume and do not necessarily converge on a single point, or isocenter, within the target). Furthermore, the treatment may be delivered in either a single session (mono-fraction) or in a small number of sessions (hypo-fractionation) as determined during treatment planning. The robotic treatment delivery system 200 delivers radiation beams according to the treatment plan without fixing the patient to a rigid, external frame to register the intra-operative position of the target volume with the position of the target volume during the pre-operative treatment planning phase The LINAC 203 is rotatably attached to the wrist assembly 212, which includes a tool-yaw joint, a tool-pitch joint, and a tool-roll joint. The tool-yaw joint of wrist assembly 212 may be coupled to a mounting plate (not illustrated), which may be attached to the bottom of the LINAC 203. Alternatively, the tool-yaw joint of wrist assembly 212 may be coupled directly to the bottom of the LINAC 203. The tool-yaw joint of wrist assembly 212 facilitates rotational movement of the LINAC 203 in a yaw-rotation along the z-axis. The tool-pitch joint may be coupled to the tool-yaw joint and facilitates rotational movement of the LINAC 203 in a pitch-rotation along the y-axis. The tool-roll joints may be coupled to the tool-pitch joint and facilitates rotational movement of the LINAC 203 in a roll-rotation along the x-axis. The z-axis, y-axis, and x-axis may be the axes 5-7 of the robotic arm 202.

In the depicted embodiment, the arm assembly includes a redundant-joint assembly 211, an elbow assembly 213, a first shoulder assembly 214, and second shoulder assembly 215. The redundant-joint assembly 211 is coupled to the tool-roll joint of the wrist assembly 212. The redundant-joint assembly 213 may include three drive shafts and three motors to drive the rotational movements of the joints of the wrist assembly

212. In one embodiment, the motors discussed herein may be step motors. Alternatively, the motors may be servo motors or other motors as would be appreciated by those of ordinary skill in the art. The first drive shaft may be coupled to the tool-yaw joint and the first motor. The first motor and drive shaft drive rotational movement of LINAC 203 along the yaw axis, axis 7. The second drive shaft may be coupled to the tool-pitch joint and the second motor. The second motor and drive shaft drive rotational movement of the LINAC 203 along the pitch axis, axis 6. The third drive shaft may be coupled to the tool-roll joint and the third motor. The third motor and drive shaft drive rotational movement of the LINAC 203 along the roll axis, axis 5. It should be noted that the axes may be designated in other orders of axes 5-7.

The elbow assembly 213 is coupled to the redundant-joint assembly 211 by a redundant joint, and the first shoulder assembly 214 is coupled to the elbow assembly 213 by an elbow joint. The redundant joint includes a gearbox, which may be configured to drive rotational movement of the redundant-joint assembly 211 in a rotational axis, axis 4. The elbow joint includes an elbow gearbox, which may be configured to drive rotational movement of the elbow assembly 213 in a rotational axis, axis 3. The shoulder assembly 214 includes a first shoulder joint, which includes a gearbox, which may be configured to drive rotational movement of the first shoulder assembly 214 in a rotational axis, axis 2. The gearboxes of the additional joint, elbow joint, and shoulder joints may facilitate translational movement of the LINAC 203 in 3-D space. The second shoulder assembly 215 is coupled to the first shoulder assembly 214 by a second shoulder joint, which includes a gearbox, which may be configured to drive rotational movement of the second shoulder assembly 215 in a rotational axis, axis 1. It should be noted that in other embodiments, the robotic arm 202 may include other types of motion actuators than gearboxes for moving the LINAC 203, in accordance with directions from the controller.

In the depicted embodiment, the redundant-joint assembly 211 is coupled between the wrist assembly 212 and the elbow assembly 213. Alternatively, the redundant-joint assembly 211 may be coupled between other components of the arm assembly. For example, in another embodiment, the redundant-joint assembly is coupled between the elbow assembly and the first shoulder assembly. In this embodiment, an elbow joint is coupled to the wrist assembly and the elbow assembly. The elbow joint includes an elbow gearbox to drive rotational movement of the robotic arm in a rotational axis, axis 4. Also, a redundant joint is coupled to the elbow assembly and the first shoulder assembly. The redundant joint includes a gearbox to drive rotational movement of the robotic arm in a rotational axis, axis 3. The first and second shoulder assemblies include the first and second shoulder joints and corresponding gearboxes to drive rotational movement of the robotic arm in the rotational axes, axis 2 and axis 1, as described above. In another embodiment, when the elbow assembly 213 is coupled directly to the wrist assembly 212, the elbow assembly includes the first, second, and third drive shafts that are coupled to the tool-yaw joint, tool-pitch joint, and the tool-roll joint, respectively, and the first, second, and third motors to drive rotational movement of the tool-yaw, tool-pitch, and tool-roll joints, respectively.

The robotic arm 202 may be coupled to a mount assembly 216 by the second shoulder joint. The mount assembly 216 may be coupled to the floor, wall, ceiling, a column, or the like. Alternatively, the robotic arm 202 may be coupled directly to the floor, wall, ceiling, a column, or the like, without the use of the mount assembly 216.

In another embodiment, the second shoulder assembly 215 includes a third shoulder joint having a third shoulder gearbox to drive rotational movement of the robotic arm in an eighth axis of the robotic arm. In another embodiment, the mount assembly 216 is coupled to a track mount assembly, which is coupled to a track 226. Alternatively, the second shoulder assembly 215 may be coupled to the track mount assembly. The track mount assembly and track may facilitate translational movement of the LINAC 203 in a substantially, linear axis. The track may be horizontally oriented or vertically oriented. This linear axis may be the eight DOF of the robotic arm. In another embodiment, the linear axis is the seventh DOF, in place of the last rotational axis, axis 1, as described above.

In one embodiment, the substantially linear DOF is a first DOF of the seven or eight DOF, meaning the DOF closest to the base end of the robotic arm, as opposed to the last DOF at the end-effector end (also referred to as the business end) of the robotic arm, which is the farthest from the base end of the robotic arm. The first DOF is configured to move the other six or seven rotational DOF of the robotic arm. That is, the medical tool and robotic arm may be moved along the substantially linear axis throughout an entire range of motion of the medical tool without movement of the medical tool along the rotational degrees of freedom.

The substantially linear DOF includes a substantially linear axis for translational movement of the medical tool along either a substantially vertical line in the z-axis substantially perpendicular to mutually orthogonal horizontal coordinate x- and y-axes or a substantially horizontal line in mutually orthogonal horizontal coordinate x- and y-axes substantially perpendicular to the z-axis. In one embodiment, the track may be vertically oriented, for example, vertically mounted to a vertical side of column. The column may be secured or mounted to the floor of the treatment room during therapeutic radiation treatment or below the floor in a pit. In another embodiment, the column may be secured or mounted to the ceiling of the treatment room during therapeutic radiation treatment. Alternatively, the track may be vertically mounted to other structures known to those skilled in the art, such as a wall, pedestal, block, or base structure. In another embodiment, the track may be horizontally oriented, for example, horizontally mounted to the floor of the treatment room during therapeutic radiation treatment or below the floor in a pit. In another embodiment, the track may be secured or mounted to the ceiling of the treatment room during therapeutic radiation treatment. Alternatively, the track may be horizontally mounted to other structures known to those of ordinary skill in the art.

In one embodiment, a controller (not illustrated for ease of illustration) is coupled to the robotic arm 202 to move the robotic arm and the LINAC 203 in the seven or more DOF. The robotic arm 202 may be controlled by motion commands received from the controller. In another embodiment, a user interface unit is coupled to the controller to manually move the robotic arm 202 and the LINAC 203 in the seven or more DOF.

The above mentioned arrangement of the wrist assembly 212, elbow assembly 213, first shoulder assembly 214, second shoulder assembly 215, and mount assembly 216 facilitate the positioning of the LINAC 203 using seven rotational DOF, including one redundant DOF. The seven DOF of the robotic arm 202 of the robotic treatment delivery system 200 may position and orient the LINAC 203 in substantially any place in a desired treatment area, such as a workspace within the mechanical range of motion of the robotic arm 202. The robotic arm 202 may position the LINAC 203 to have a tool center position (TCP), machine center, or isocenter in multiple locations within the workspace or treatment area. The motion command signals, generated by the controller, may control corrective motions of the robotic treatment delivery system 200 in the various DOF. In one embodiment, the position and orientation of the LINAC 203 with respect to the treatment couch 206 may be known, so that coordinated movements may be effected. In one exemplary embodiment, both the LINAC 203 and the treatment couch 206 can be referenced to a common (or "room") coordinate system. Alternatively, the robotic arm 202 may be configured to facilitate motion of the LINAC 203 along eight DOF.

In one embodiment, the eight DOF include two redundant DOF. In another embodiment, the eight DOF include seven rotational DOF, including one redundant DOF, and one translational DOF. Alternatively, other configurations are possible. In one exemplary embodiment, the seven DOF includes four rotational axes for translational movement of the LINAC 203 along mutually orthogonal x-, y-, and z-coordinate axes, and three rotational axes for roll-, pitch-, and yaw-rotations of the LINAC 203 about x-, y-, and z-axes, respectively. In this embodiment, the four rotational axes include one redundant rotational axis for translational movement of the LINAC 203. In another exemplary embodiment, the eight DOF includes five rotational axes for translational movement of the LINAC 203 along mutually orthogonal x-, y-, and z-coordinate axes, and three rotational axes for roll-, pitch-, and yaw-rotations of the LINAC 203 about x-, y-, and z-axes, respectively.

In another exemplary embodiment, the eight DOF includes four rotational axes for translational movement of the LINAC 203 along mutually orthogonal x-, y-, and z-coordinate axes, three rotational axes for roll-, pitch-, and yaw-rotations of the LINAC 203 about x-, y-, and z-axes, respectively, and a substantially linear DOF that includes a substantially linear axis for translational movement of the medical tool along either a substantially vertical line in the z-axis substantially perpendicular to mutually orthogonal horizontal coordinate x- and y-axes or a substantially horizontal line in mutually orthogonal horizontal coordinate x- and y-axes substantially perpendicular to the z-axis. Alternatively, one or more redundant DOF may be used in other configurations.

The robotic treatment delivery system 200 is configured to adjust the position and orientation of the LINAC 203 in a 3D workspace or operating envelop in a treatment room under computer control, during therapeutic radiation treatment, using the controller. The controller may be coupled to the robotic arm 202, a motion tracking system 210, a user interface, an imaging system (including x-ray sources 207 and detectors 208), and a patient positioning system 212, including a treatment couch 206. Alternatively, the controller is coupled to more or less components of the system depicted in FIG. 1.

In one embodiment, the robotic treatment delivery system 200 may be a frameless, image-guided robot-based therapeutic radiation treatment system utilizing a LINAC. Alternatively, the robotic treatment delivery system 200 may be other types of robot based medical systems. In one embodiment, the radiation source is a LINAC, such as LINAC 203. Alternatively, the radiation source may be other types of radiation sources that can be mounted to the distal end of the robotic arm. In one embodiment, the LINAC 203 is an x-ray LINAC. Alternatively, the LINAC 203 may be other types of LINACs as would be appreciated by those of ordinary skill in the art.

In the depicted embodiment, the patient positioning system 212 includes the treatment couch 206 coupled to a robotic arm 221 having a wrist assembly 222, an elbow assembly 223, a shoulder assembly 224, a track mount assembly 225, and a track 226. The robotic arm 221 is configured to move the treatment couch in six DOF, including one substantially linear DOF. The robotic arm 221 includes multiple rigid links, interconnected by joints, to move the treatment couch 206 in the five rotational DOF. The robotic arm 221 is mounted to the track 226, which facilitates movement of the treatment couch 206 in the substantially linear DOF. The wrist assembly 222 is configured to move the treatment couch 206 in three rotational DOF (Axes 4-6), and the elbow, shoulder, and track mount assemblies 223-225, and the track 226 are configured move the treatment couch 206 in three DOF, two rotational DOF and the substantially linear DOF.

The elbow assembly 223 is coupled to the wrist assembly 222 and the shoulder assembly 224. The track mount assembly 225 is coupled to the track 226 and to the shoulder joint of the shoulder assembly 214. In the depicted embodiment, the track mount assembly 225 and track 226 facilitate translational movement of the LINAC 203 in a substantially vertical, linear axis. The substantially vertical, linear axis (z-) may be substantially perpendicular to the two dimensional horizontal plane (x-, y-). In one embodiment, the track may be vertically oriented, for example, vertically mounted to a vertical side of a column. The column may be secured or mounted to the floor of the treatment room during therapeutic radiation treatment or below the floor in a pit. In another embodiment, the column may be secured or mounted to the ceiling of the treatment room during therapeutic radiation treatment. Alternatively, the track 226 may be vertically mounted to other structures known to those skilled in the art, such as a wall, pedestal, block, or base structure.

Although the treatment couch 206 is coupled to the robotic arm 221 in FIG. 1, in other embodiments, other patient positioning systems may be used to position and orient the patient relative to the robotic treatment delivery system 200. For example, the LINAC 203 may be positioned with respect to a treatment couch 206 that is not coupled to a robotic arm, such as a treatment couch mounted to a stand, to the floor, to the AXUM® treatment couch, developed by Accuray Inc., of Sunnyvale, Calif., or to other patient positioning systems.

In one embodiment, the robotic arm 221 is coupled to the same controller as the controller that controls the robotic arm 202. The controller may be used to coordinate the movements of both the LINAC 203 and the treatment couch 206 relative to one another. This may allow the LINAC 203 to be positioned and oriented with respect to the treatment couch in additional positions that may have been previously obstructed for conventional systems. In another embodiment, the robotic arms 202 and 221 are coupled to separate controllers.

In another embodiment, the robotic treatment delivery system 200 includes an x-ray imaging system. The x-ray imaging system generates image data representative of one or more real time or near real time images of the target. The x-ray imaging system may include a pair of diagnostic x-ray sources 207, power supplies associated with each x-ray imaging source, one or two imaging detectors 208 (or cameras), and controller. The x-ray imaging sources 207 may be mounted angularly apart, for example, about 90 degrees apart, and aimed through the treatment target (e.g., tumor within the patient) toward the detector(s) 208. Alternatively, a single large detector may be used that would be illuminated by each x-ray source. In the single detector imaging system, the two x-ray sources 207 may be positioned apart at an angle less than 90 degrees to keep both images on the single detector surface.

The detector(s) 208 may be placed below the treatment target, e.g., on the floor, on the treatment couch 206, or underneath the LINAC 203, and the x-ray imaging sources 207 may be positioned above the treatment target (e.g. the ceiling of the treatment room), to minimize magnification of the images and therefore the required size of the detector(s) 208. In an alternative embodiment, the positions of the x-ray imaging sources 207 and the detector(s) 208 may be reversed, e.g. the x-ray imaging sources 207 below the treatment target and the detector(s) 208 above the treatment target. In another embodiment, the detector(s) 208 are arranged in a manner such that they move into position for imaging and the moved out of the way during positioning of the LINAC 203 or the treatment couch 206 or during delivery of the radiation beam from the LINAC 203.

The detector(s) 208 may generate the image information of the patient and send it to the controller. The controller performs all the imaging calculations to determine the patient's position with respect to the desired treatment position and generate corrections for the various DOF. The corrections could be automatically applied to the robotic treatment delivery system 200 to automatically align the LINAC 203, and/or sent to the controller to automatically adjust the patient's position using the treatment couch 206 and robotic arm 212 relative to the LINAC 203, and/or sent to the user interface unit for a user to manually adjust the patient's position relative to the LINAC 206, using one or both of the robotic arms 202 and 221.

In another embodiment, the corrective motions of the robotic treatment delivery system 200 may be dynamically coordinated with the motions of the treatment couch 206 and robotic arm 221 using the controller, in a way as to maximize the workspace available to the system. By dynamically coordinating the motions of the treatment couch 206 and the LINAC 203 using the controller, the available number of treatment targets increases due to the increased number of orientations and positions of the LINAC 203 and the treatment couch 206, which are free of obstructions, for example, by detectors 208 and/or x-ray imaging sources 207, robotic arms, or other equipment within the treatment room. In this embodiment, the robot-implemented movements of the LINAC 203 are complemented by the corrective motions of the treatment couch 206, so that the relative motion between the LINAC 203 and the treatment couch 206 ensures the delivery of the desired radiation pattern throughout the target region.

The treatment couch 206 supports the patient 205 during treatment, and may be positioned between the two x-ray cameras and their respective diagnostic x-ray sources of the imaging system. In one embodiment, the treatment couch 206 may be made of a radiolucent material so that the patient could be imaged through the treatment couch 206.

The imaging system generates, in real time or near real time, x-ray images showing the position and orientation of the target in a treatment coordinate frame. The controller may contain treatment planning and delivery software, which may be responsive to pre-treatment scan data CT (and/or MRI data, PET data, ultrasound scan data, and/or fluoroscopy imaging data) and user input, to generate a treatment plan consisting of a succession of desired beam paths, each having an associated dose rate and duration at each of a fixed set of treatment positions or nodes. In response to the controller's directions, the robotic arm moves and orients the LINAC 203, successively and sequentially through each of the nodes, while the LINAC 203 delivers the required dose as directed by the controller. The pre-treatment scan data may include, for example, CT scan data, MRI scan data, PET scan data, ultrasound scan data, and/or fluoroscopy imaging data.

Prior to treatment, the patient's position and orientation within the frame of reference established by imaging system may be adjusted to match the position and orientation that the patient had within the frame of reference of the CT (or MRI or PET or fluoroscopy) scanner that provided the images used for planning the treatment. In one exemplary embodiment, this alignment may be performed to within tenths of a millimeter and tenths of a degree for all of the DOF.

The controller may also communicate with a diagnostic or treatment planning system, receiving pre-treatment scan data representative of one or more pre-treatment scans of a treatment target within the patient. The pre-treatment scans may show the position and orientation of the target with respect to a pre-treatment coordinate system. The controller may also receive from the imaging system (x-ray sources 207 and detectors 208) image data representative of real time or near real time images of the target. The image data may contain information regarding the real time or near real time position and orientation of the target with respect to a treatment coordinate system. The treatment coordinate system and the pre-treatment coordinate system are related by known transformation parameters.

The controller may include an input module for receiving 1) pre-treatment scan data representative of pre-treatment scans of the target, and 2) real time or near real time image data representative of real time or near real time images of the target. The pre-treatment scans show the position and orientation of the target with respect to the pre-treatment coordinate system. The near real-time images, taken by the imaging system under the command of the controller, show the position and orientation of the treatment target with respect to the treatment coordinate system. The treatment coordinate system and the pre-treatment coordinate systems are related by known transformation parameters. The controller includes a TLS (target location system) processing unit that computes the position and orientation of the treatment target in the treatment coordinate system, using the pre-treatment scan data, the real time or near real time image data, and the transformation parameters between the pre-treatment coordinate system and the treatment coordinate system. The processing unit of the controller may also compute the position and orientation of the isocenter of the LINAC 203.

The motion tracking system 210 may be used for detecting the position of the LINAC 203 and/or a treatment couch 206. The motion tracking system 210 may be a part of, or separate from the robotic treatment delivery system 200. The controller may be operatively coupled to motion tracking system 210 in order to calculate the position and orientation of the LINAC 203 relative to the treatment room or other predefined treatment coordinate system based on the data received from the motion tracking system. The controller may independently check the position and orientation of the LINAC against a model of surrounding obstructions to ensure that the LINAC 203 does not collide with obstacles during motion of the robotic treatment delivery system 200. The controller may also operate to control the motion of the robotic treatment delivery system 200 in a way that a treatment target within the patient's anatomy remains properly aligned with respect to a treatment beam source of the LINAC 203 throughout the treatment procedure. Controller may also be used to operate the positioning of the treatment couch 206.

The motion tracking system 210 may be a laser scanning system or an optical tracking system disposed within the treatment room for detecting the position of the LINAC 203 relative to the treatment room or other treatment coordinate system. An exemplary laser scanning system may scan the treatment room approximately 60×/sec to determine the position of the LINAC 203. The laser scanning system may include devices performing a single plane scanning, or two-plane scanning, or multiple-plane scanning. Correspondingly, the controller may be loaded with software adapted for receiving information from the motion tracking system 210 and calculating the position of the LINAC 203, as well as the treatment couch or other equipment in the treatment room, so that the robotic treatment delivery system 200 including the controller always knows the position of the LINAC 203. The controller may be programmed to automatically or periodically calibrate the LINAC 203 with the treatment couch.

In an alternative embodiment, the motion tracking system 210 includes a magnetic tracking system for tracking the position of the LINAC 203 relative to the treatment coordinate system. The magnetic tracking system preferably includes at least one transducer attached to the LINAC 203. Alternatively, other sensor systems may be used, such as an inertial sensor attached to the LINAC 203 for sensing the motions of the LINAC 203, a resolver-based sensor system, an infrared triangulation system, an optical encoder, or the like, as would be appreciated by those of ordinary skill in the art. It should be noted that the motion tracking system 210 may be used for tracking the robotic arm 202, LINAC 203, robotic arm 221, the treatment couch 206, a patient 205, or other objects within the treatment room. The motion tracking system 210 may also be used for tracking a target within the patient 205.

The controller may be adapted to detect a misalignment of the treatment target with the isocenter of the LINAC 203 caused by patient's movement by comparing the position of the treatment target with the isocenter of the LINAC 203, and generate motion command signals for implementing corrective motions of the robotic treatment delivery system 200 for aligning the treatment target with respect to the radiation treatment source (e.g., LINAC 203).

In another embodiment, the corrective motions of the robotic treatment delivery system 200 may accommodate for various motions, such as respiratory motion; cardiac pumping motion of the patient's heart; sneezing, coughing, or hiccupping; and muscular shifting of one or more anatomical members of the patient. In another embodiment, the robotic treatment delivery system 200 including the controller may be adapted to detect and accommodate changes in tumor geometry that may be caused by tissue deformation by comparing the real time or near real time image with the pre-treatment image and repositioning the LINAC 203 using the robotic arm 202 and/or the patient using the treatment couch, or adjusting the positions of the LINAC 203 and the treatment couch to correspond to the treatment plan.

The controller includes software for establishing and maintaining a reliable communication interface with the LINAC 203. The software uses the interface specifications developed for the LINAC 203. The controller further includes software for converting the patient position and orientation information from the imaging system to appropriate units of movement in the DOF of motion capability of the LINAC 203. The controller may include software for providing a user interface unit to the treatment delivery system's user control console, to monitor and initiate the motion of the robotic treatment delivery system 200 for positioning the patient. The controller 200 may also include software for detecting, reporting, and handling errors in communication or software control of the LINAC 203.

The controller may include at least one user interface unit for enabling the user to interactively control the motions or corrective motions of the robotic treatment delivery system 200, by implementing one or more user-selectable functions. The user interface unit may be a handheld user interface unit or remote control unit. Alternatively, the user interface unit may be a graphical user interface (GUI) on a display.

The communication links between the controller and other components of the robotic treatment delivery system 200 (e.g., the robotic arm 202, LINAC 203, motion tracking system 210, user interface, treatment couch 206, and imaging system) may be wired links or wireless links, with a bandwidth necessary for maintaining reliable and timely communications.

It should be noted that additional joint in the embodiments above has been implemented in a redundant-joint assembly that is coupled between the wrist assembly 211 and the elbow assembly 213, however, in other embodiments, the redundant joint may be implemented in other configurations. In one embodiment, the robotic arm includes a wrist assembly that is coupled to the LINAC 203, and an arm assembly that is coupled to the wrist assembly. The arm assembly may include one or more redundant joints. The one or more redundant joints may be implemented in conjunction with one or more redundant-joint assemblies, or as additional joints to the other assemblies of the arm assembly. For example, the depicted embodiment of FIG. 1 illustrates the additional joint between the wrist assembly 211 and the elbow assembly 213. In other embodiments, the additional joint may be disposed in a redundant-joint assembly coupled between any two of the following: the elbow assembly 213, first shoulder assembly 214, second shoulder assembly 215, and the mount assembly 216. In other embodiments, the additional joint may be implemented as an additional joint to a joint of any one of the following: the elbow assembly 213, first shoulder assembly 214, and second shoulder assembly 215. For example, the first and second shoulder assemblies (collectively with the mount assembly 216 may be referred to as a base assembly) includes the first and second shoulder joints. The additional joint may be added at the location of the first and second axes (A1 and A2) (e.g., at the base assembly including the first and second shoulder joints). By adding the additional joint at the location of the first and second shoulder joints, the arm assembly is capable to position the joints such that a greater range of motion is capable without putting the patient or treatment couch in danger of collision with the robotic arm or LINAC 203, as compared to the conventional robotic arm. Also, by adding the additional joint at the location of the first and second shoulder joints, the arm assembly is capable of rotating the bulk of the robotic arm, for example, towards the floor, as illustrated in FIG. 2.

Figure 2:
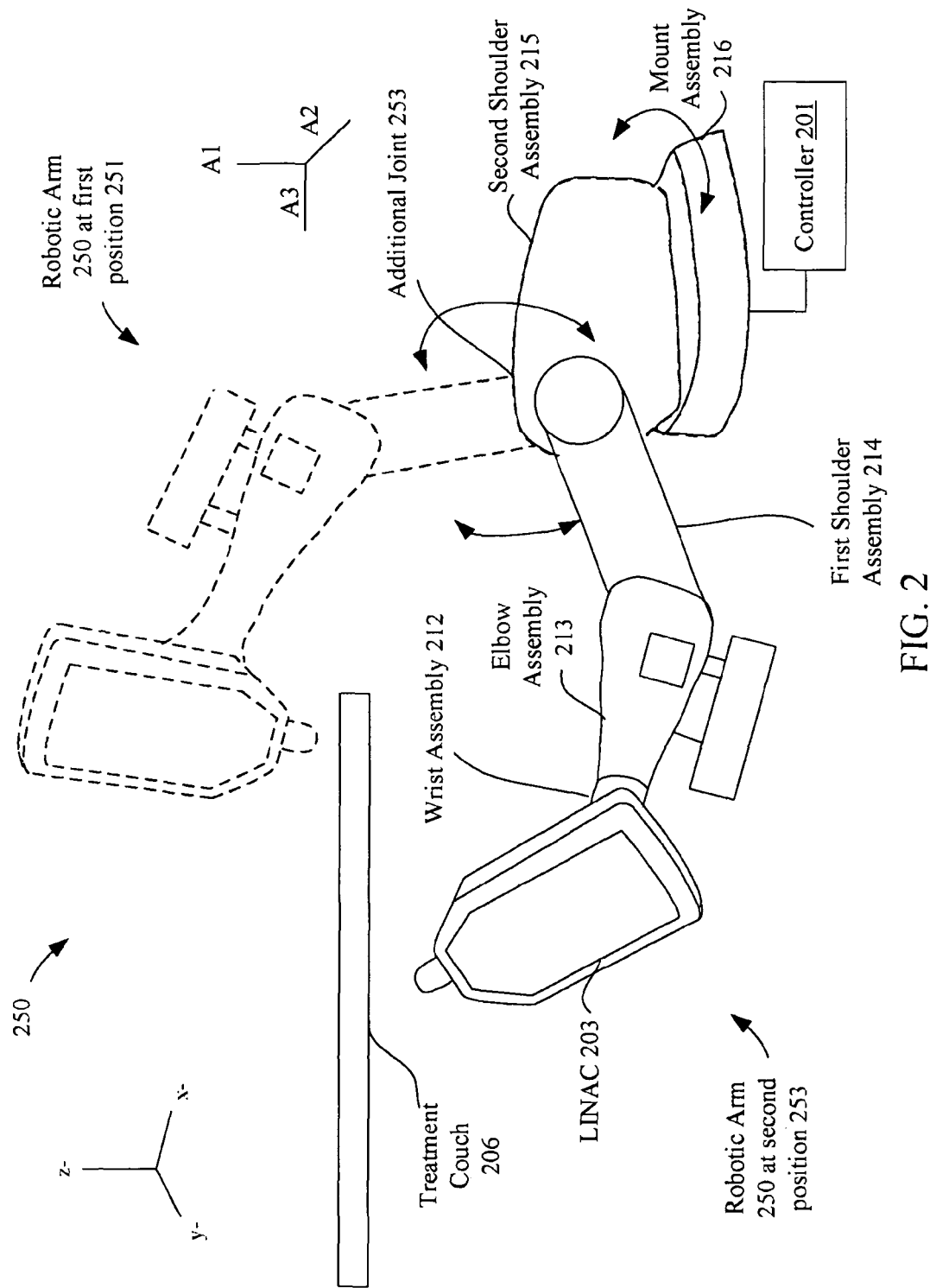
FIG. 2 illustrates another embodiment of a robotic treatment delivery system having a redundant joint.

FIG. 2 illustrates another embodiment of a robotic treatment delivery system 250 having a redundant joint. The robotic treatment delivery system 250 includes the LINAC 203 coupled to a robotic arm 252. The robotic arm 252 includes the wrist assembly 212, elbow assembly 213, first shoulder assembly 214, second shoulder assembly 215, and the mount assembly 216, as described above with respect to FIG. 1. Rather than having the redundant-joint assembly 211, the robotic arm 252 includes an additional joint 253 at the location of the first and second shoulder assemblies. It should be noted that the robotic arm 202 uses the first and second shoulder joints to move the robotic arm 202 along the first and second rotational axes (A1 and A2) at the base assembly and the elbow and redundant joints to move the robotic arm 202 along the third and fourth rotational axes (A3 and A4). The arm assembly of the robotic arm 202 includes the base assembly, which includes the first and second shoulder joints, and three rigid links interconnected by the additional joint and the elbow joint. In contrast, the robotic arm 252 uses the first and second shoulder joints, and the additional joint 253 to move the robotic arm 252 along the first, second, and third rotational axes (A1, A2, and A3) at the base assembly, and the elbow joint to move the robotic arm 252 along the fourth rotational axis (A4). The arm assembly of the robotic arm 252 includes the base assembly, which includes the first and second shoulder joints and the additional joint 253, and two rigid links interconnected by the elbow joint. As described above, by adding the additional joint 253 at the base assembly, the bulk of the robotic arm 252 may be rotated, for example, towards the floor.

In the depicted embodiment, the robotic arm 250 is rotated from a first position 251 (indicated by dashed lines), to a second position 253 (indicated by solid lines). These two positions 251 and 252 may be used to position the LINAC 203 to a high position for treating lower isocenters, and to a low position for treating higher isocenters. For example, the treatment couch 206 in FIG. 2 has been illustrated as being disposed in a high position. As such, the isocenter may be a high isocenter. In order to position the LINAC 203 in certain positions below the high isocenter, the robotic arm 252 may be rotated about the additional joint 253 to position the LINAC 203 underneath the high isocenter, such as at the second position 253. However, when the treatment couch 206 is moved to a lower position, the robotic arm 252 may be rotated about the additional joint 253 to position the LINAC 203 above the low isocenter, such as at the first position 251.

Although the embodiments above are described as moving the LINAC 203 and robotic arm 202 with respect to the treatment couch 206, which is coupled to a robotic arm 221, in other embodiments, the LINAC 203 and robotic arm 202 are moved with respect to a conventional treatment couch 106, which may be coupled to a conventional robotic arm, such as robotic arm 102, or a conventional treatment couch that is not coupled to a conventional robotic arm.

The embodiments of FIGS. 1 and 2 illustrate robotic arms that are mounted horizontally to a mount assembly, as well as to the floor. In other embodiments, the robotic arms, including one or more additional joints may be vertically mounted, such as illustrated in FIGS. 3A and 3B.

Figure 3A:
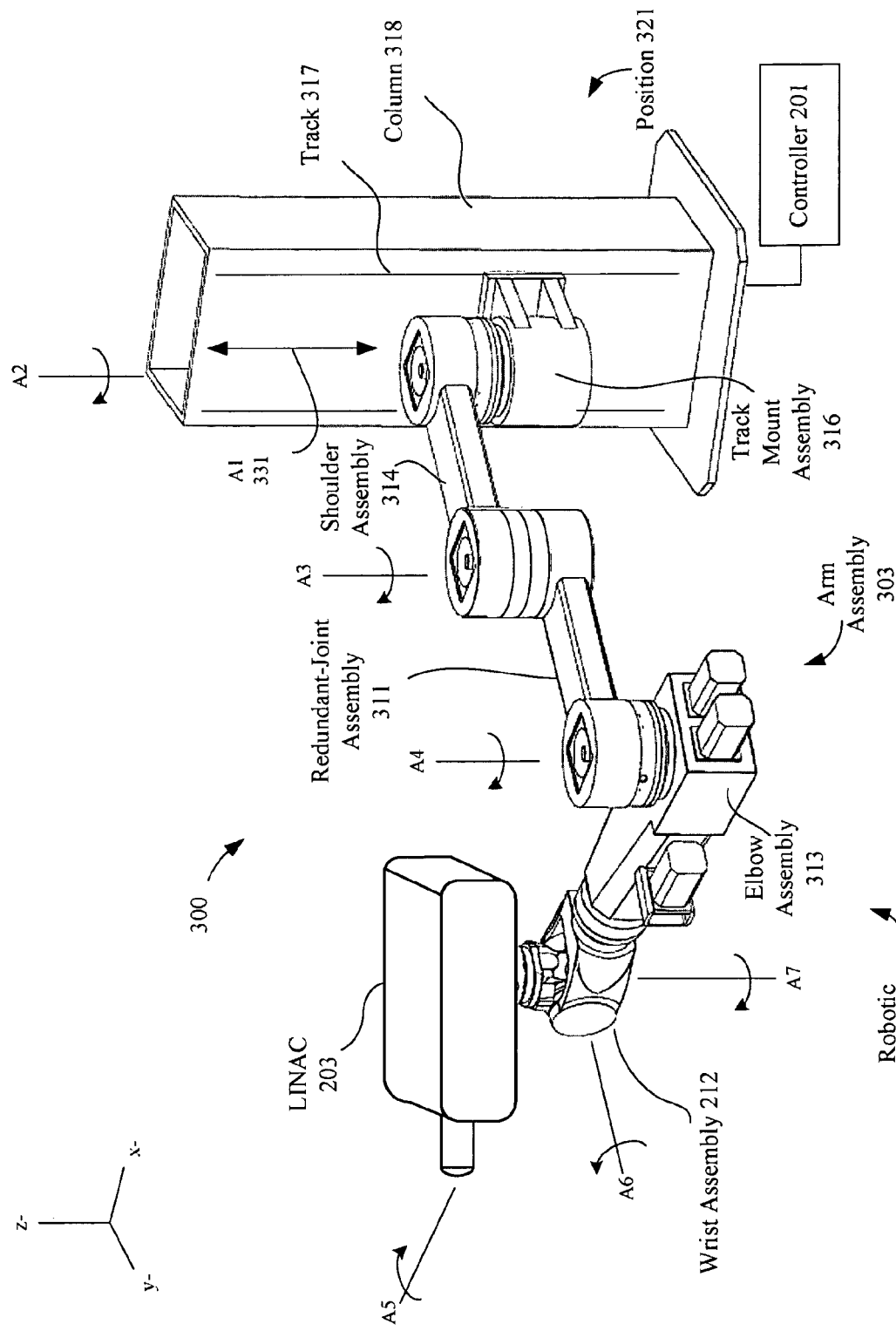
FIG. 3A illustrates one embodiment of a robotic treatment delivery system 300 including a vertically-mounted robotic arm having seven degrees of freedom in a first position along the first axis.
Figure 3B:
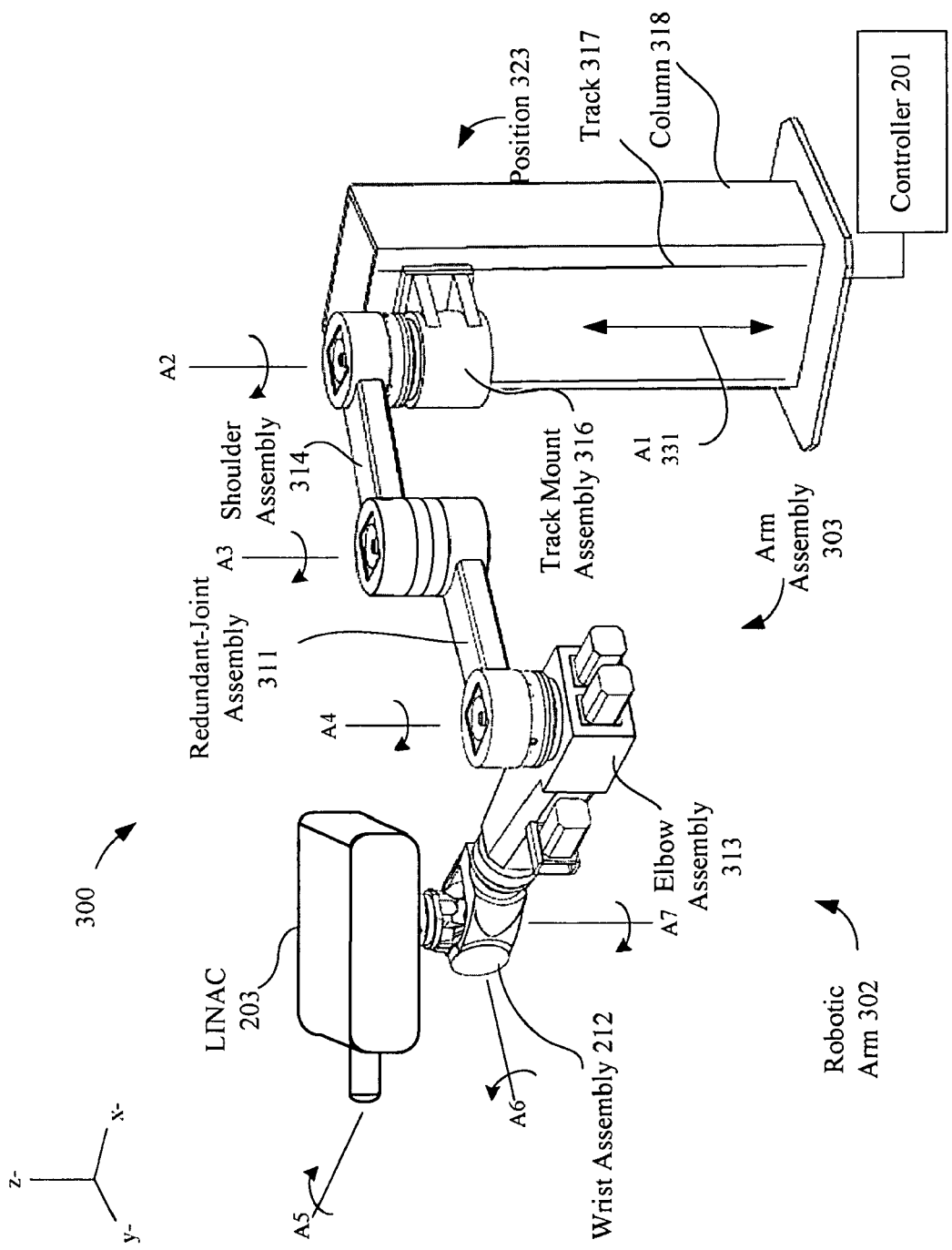
FIG. 3B illustrates another embodiment of the robotic treatment delivery system of FIG. 3A in a second position along the first axis.

FIGS. 3A and 3B illustrates one embodiment of a robotic treatment delivery system 300 including a vertically-mounted robotic arm having seven degrees of freedom in two positions 321 and 323 along the first axis. The robotic treatment delivery system 300 includes the LINAC 203 coupled to the robotic arm 302. The robotic arm 302, like robotic arms 202 and 252, includes the wrist assembly 212 and an arm assembly. As described above, the wrist assembly 212 is configured to move the LINAC 203 in three rotational DOF (Axes 5-7). The depicted embodiment of the arm assembly of FIG. 3A includes an elbow assembly 313, a redundant-joint assembly 311, a shoulder assembly 314, a track mount assembly 316, and track 317. The elbow assembly 313 is coupled to the tool-roll joint of the wrist assembly 212. The elbow assembly 313 may include three drive shafts and three motors, as described above with respect to the redundant-joint assembly 211. The redundant-joint assembly 311 is coupled to the elbow assembly 313 by an elbow joint, and to the shoulder assembly 314 by a redundant joint. The shoulder assembly 314 is coupled to the track mount assembly 316 by a shoulder joint. The elbow joint, redundant joint, and shoulder joint may include a gearbox, which may be configured to drive rotational movement of the elbow assembly 313 in a fourth rotational axis (axis 4), the redundant-joint assembly 311 in a third rotational axis (axis 3), and the shoulder assembly 314 in a second rotational axis (axis 2), respectively. The gearboxes of the elbow joint, redundant joint, and shoulder joint may facilitate translational movement of the LINAC 203 in a two-dimensional horizontal plane, for example, in the (x-, y-) plane parallel with the floor. The track mount assembly 316 and track 317 facilitate translational movement of the LINAC 203 in a substantially vertical, linear axis (axis 1). The substantially vertical, linear axis (z-) may be substantially perpendicular to the two dimensional horizontal plane (x-, y-).

In this embodiment, the track 317 is mounted to a vertical side of a column 318. The column 318 may be secured or mounted to the floor of the treatment room during therapeutic radiation treatment or below the floor in a pit. In another embodiment, column 318 may be secured or mounted to the ceiling of the treatment room during therapeutic radiation treatment. Alternatively, the track 317 may be vertically mounted to other structures known to those skilled in the art, such as a wall, pedestal, block, or base structure.

A controller 201 is coupled to the robotic arm 302 to move the robotic arm 302 and the LINAC 203 in the seven DOF. The robotic arm 302, controlled by the controller 201, facilitate the positioning and orienting of the LINAC 203 using six rotational DOF, and one translational substantially vertical, linear DOF. Like the robotic arm 202, the six rotational and one substantially horizontal, linear DOF of the robotic arm 302 of the robotic treatment delivery system 200 may position the LINAC 203 in substantially any place in a desired treatment area, such as a workspace, within the mechanical range of motion of the robotic arm 302. The robotic arm 302 may position the LINAC 203 to have a TCP in multiple locations within the workspace or treatment area.

In one embodiment, the robotic arm 302 is configured to move the LINAC 203 along a single axis without moving the LINAC 203 along the other axes throughout an entire range of motion of the LINAC 203. For example, the first DOF is configured to move the LINAC 203 along a substantially linear axis through substantially an entire range of motion of the robotic arm without movement of the LINAC 203 along the four, five, or six rotational DOF. The first DOF is the DOF that is closest to the base end of the robotic arm. The base end is where the robotic arm 302 is mounted to the column 318. Alternatively, the base end is where the robotic arm 302 is mounted to the floor, ceiling, wall, or other mounting locations in the treatment room. The LINAC 203 is coupled to the robotic arm 202 at the end-effector end of the robotic arm 302, also referred to as the business end of the robotic arm 302.

In one embodiment, the controller 201 is configured to move the robotic arm 302 in along the first axis 331 of the first DOF. The first DOF is configured to move the other six rotational DOF of the robotic arm 302. The controller moves the robotic arm 302 up and down along the axis 331 to different positions. For example, the robotic arm 302 may be positioned in the first position 321, as illustrated in FIG. 3A, and in the second position 323, as illustrated in FIG. 3B. As illustrated in FIGS. 3A and 3B, the robotic arm 302 can be configured to move the LINAC 203, as well as the robotic arm 302, along the substantially vertical, linear axis (e.g., axis 331) throughout substantially an entire range of motion of the LINAC 203 without movement of the LINAC 203 along the six rotational DOF.

In another embodiment, the robotic arm 302 has a substantially linear DOF that is horizontal. In another embodiment, the robotic arm 302 has four rotational DOF and one substantially linear DOF, and the first DOF is the substantially linear DOF that is configured to move the other four rotational DOF of the robotic arm. In this embodiment, the controller can move the LINAC along the substantially linear axis (e.g., axis 331 or a horizontal first axis) throughout substantially an entire range of motion of the LINAC 203 without movement of the LINAC 203 along the four rotational DOF. In the embodiment of the first DOF being horizontal, the controller is configured to move the LINAC 203 along a substantially horizontal line in the mutually orthogonal horizontal coordinate axes (e.g., x- and y-axes) that are substantially perpendicular to the vertical axis (e.g., z-axis). In the embodiment of the first DOF being vertical, the controller is configured to move the LINAC 203 along a substantially vertical line in the vertical axis (e.g., z-axis) that is substantially perpendicular to the mutually orthogonal horizontal coordinate axes (e.g., x- and y-axes).

Figure 3C:
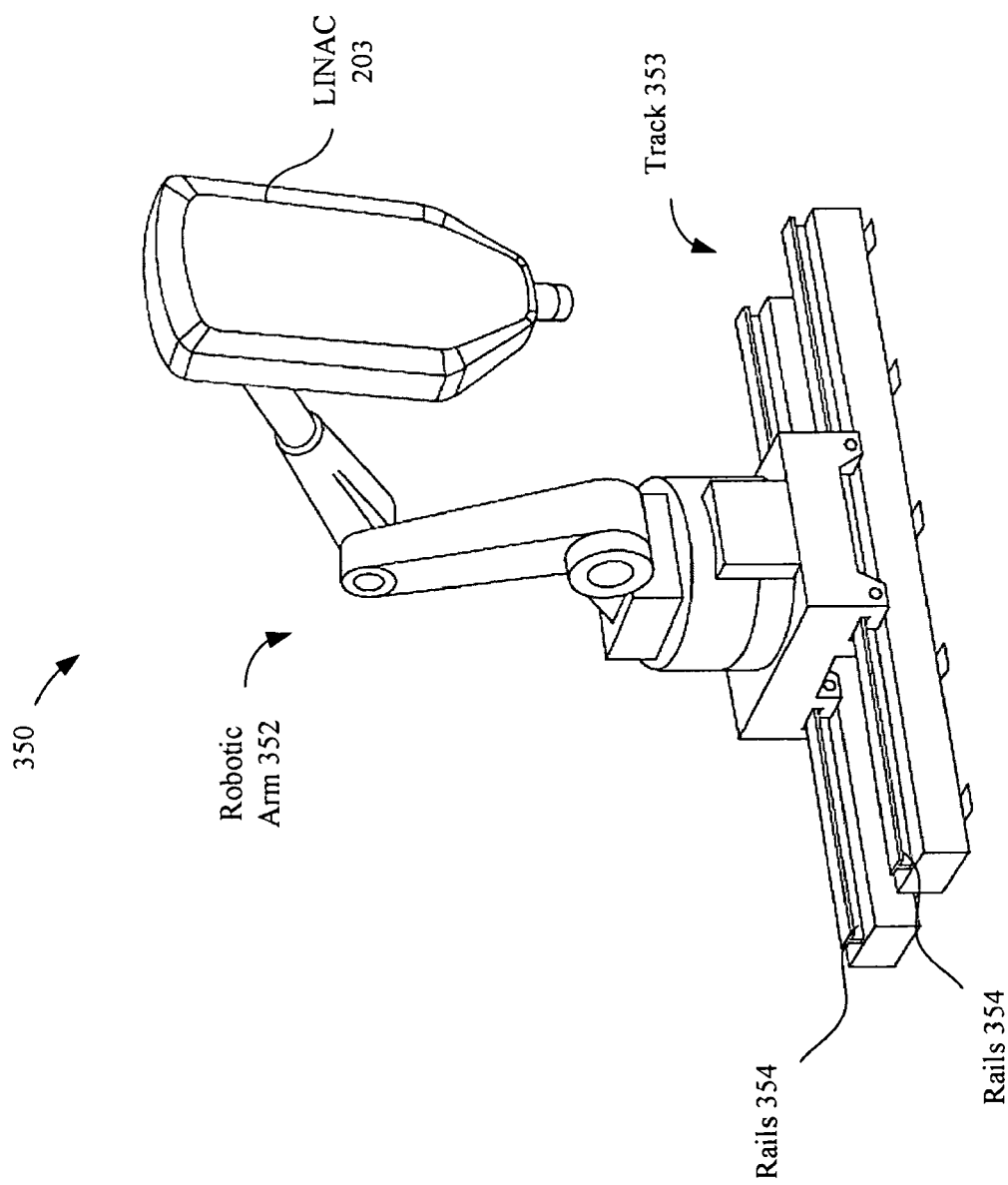
FIG. 3C illustrates another embodiment of a robotic treatment delivery system 350 including a robotic arm having six degrees of freedom horizontally mounted on a linear track for a seventh degree of freedom.

FIG. 3C illustrates another embodiment of a robotic treatment delivery system 350 including a robotic arm having six degrees of freedom horizontally mounted on a linear track 353 for a seventh degree of freedom. It should be nod that although the linear track 353 is described as the seventh DOF, the linear track 353 can also be referred to the first DOF, since the first DOF is typically the DOF closest to the base end of the robotic arm 352. The linear track 353 allows the entire robotic arm 352 to be moved from one position to another in the treatment room, providing a seventh DOF in addition the six DOF of the robotic arm 352. The robotic treatment delivery system 350 includes a horizontally-mounted robotic arm 352 having six degrees of freedom, and the LINAC 203 coupled to the robotic arm 352. The robotic arm 352 is horizontally mounted to a linear track 353 having, for example, rails 354 that allow the robotic arm 352 to be translated along a linear axis. The robotic arm 352 may be coupled to a track mount assembly that engages with the rails 354 to allow the robotic arm 352 to be moved along the track 353. Alternatively, other types of mechanism may be used to allow the robotic arm 352 to be moved along the track 353, as would be appreciated by one of ordinary skill in the art. In another embodiment, the track 353 is a non-linear track. The controller (not illustrated) is configured to move the robotic arm 352 and the LINAC 203 in the seven DOF, including one translational DOF (e.g., substantially horizontal), and the six rotational DOF of the robotic arm 352. The controller can move the robotic arm 352 along a single axis (or non-linear path) without moving the other DOF of the robotic arm 352 throughout an entire range of motion of the LINAC 203. In effect, the seventh DOF allows the entire frame of reference to be shifted.

Although the embodiment described above is a horizontally-mounted, six DOF robotic arm 352 that is mounted to a floor, other configurations are possible. For example, the linear track 353 may be mounted to a ceiling or to a pit within the floor. Also, in other embodiments, the track may be vertically mounted to a column, a wall, or the like. In other embodiments, the robotic arm 352 includes a redundant degree of freedom, as described herein. In one embodiment, the robotic arm 352 includes six degrees of freedom, one of the six being a redundant DOF, and the seventh DOF is the track. In another embodiment, the robotic arm 352 includes seven DOF, one of the seven being a redundant DOF, and the eighth DOF is the track. Alternatively, the robotic arm 352 may include more than one redundant DOF.

Using just a six DOF robotic arm, the workspace, which is representative of the operating envelop of the robotic arm may be non-symmetric about the patient because of interference and reachability issues. For example, if the robotic arm is disposed on one side of the patient, the LINAC may not be positioned in certain positions because it would be obstructed by the patient, the treatment couch, or other objects within the room. The linear track 353 can enable the robotic arm 353 to be positioned on both sides of the treatment couch, creating a symmetric workspace. The linear track 353 may also enable an expanded workspace, allowing the LINAC 203 to be positioned in more positions that were previously obstructed or avoided due to the proximity of the patient. The linear track 353 may also expand the workspace by moving the robotic arm 353 closer to or further away from the patient. This may be analogous to someone lifting a heavy object wither with one's arm stretched out or too close to one's body. If it's too close, one might step farther away, and if it's too far away, one might step closer to the object. Since uniquely positioning the LINAC 203 in space may be done with the six DOF, the flexibility provided by the seventh DOF (e.g., track) can be used for positioning the robotic arm 352 to avoid obstacles or other interferences in the treatment room, for a given position of the LINAC 203. The seventh DOF may also provide more desirable positions for the robotic arm 352, for example, to avoid reaching over and across the patient. The seventh DOF may also optimize time of travel based on positions of the robotic arm 352. For example, the robotic arm 352 may be moved along the linear DOF without moving the other DOFs. It should be noted that all of these capabilities may be performed at the same time, but in one embodiment, the controller may go through a list of these capabilities according to priority, such as an ordered list.

The treatment delivery systems 300 and 350 may be used in conjunction with an imaging system, a motion tracking system, and a patient positioning system, as described with respect to FIG. 1.

In one embodiment, components of the robotic arm 202 or robotic arm 302 may include touch-sensing material on the components' exterior. In another embodiment, the exterior of the components may be coated with contact foam. Alternatively, other materials may be used to prevent components of the robotic arm 202 or 302 from crushing or knocking over the operator. Specific details regarding the touch-sensing material and contact foam that are known to those of ordinary skill in the art have not been included as to not obscure the discussion regarding coating the exterior of the robotic arms 202 and 302 with material to prevent the operator from being knocked over or crushed by the robotic arms.

In one embodiment, the robotic arms of FIGS. 1, 2, 3A, and 3B may include components manufactured by KUKA Roboter GmbH of Germany. Alternatively, the components of the robotic arms may include other types of components.

Figure 4B:
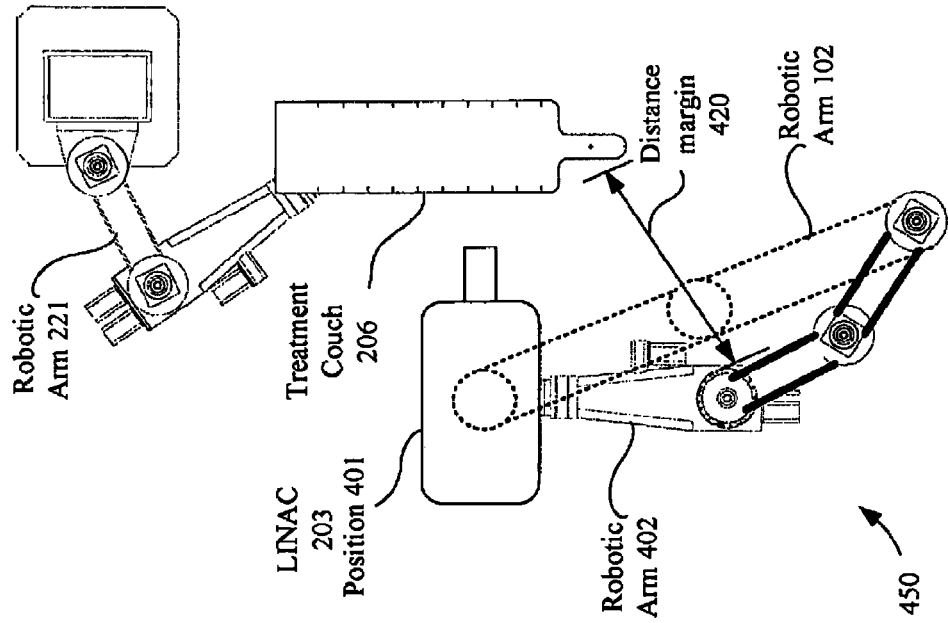
FIG. 4B illustrates a top side view of a robotic treatment system in the first position relative to the treatment couch, according to one embodiment.
Figure 4A:
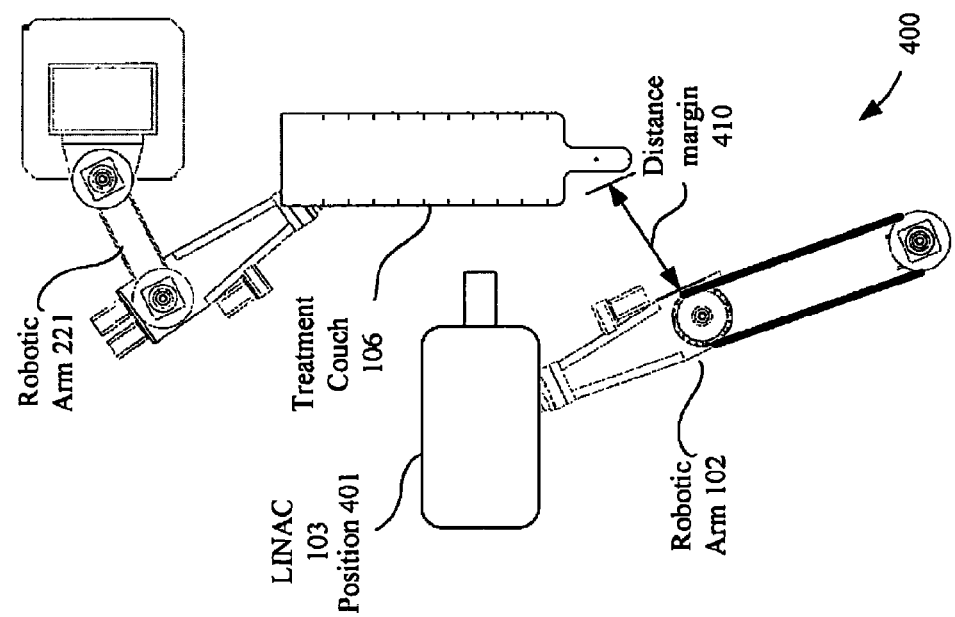
FIG. 4A illustrates a top side view of a conventional robotic treatment delivery system in a first position relative to a treatment couch.

FIG. 4A illustrates a top side view of a conventional robotic treatment delivery system 400 in a first position 401 relative to the treatment couch 206. The conventional robotic treatment delivery system 400 includes the LINAC 103 coupled to the robotic arm 102. The robotic arm 102 has two rigid links interconnected by a single elbow joint. The LINAC 103 has been positioned to the first position 401 relative to the treatment couch 206. At the first position 401, there is a distance margin 410 between the treatment couch 206 and the LINAC 103 and robotic arm 102.

FIG. 4B illustrates a top side view of a robotic treatment system 450 in the first position 401 relative to the treatment couch 206, according to one embodiment. The robotic treatment delivery system 450 includes the LINAC 203 coupled to the robotic arm 402. The robotic arm 402, unlike the robotic arm 102, has three rigid links interconnected by two joints, an elbow joint, and a redundant joint. The robotic arm 102 has been illustrated (dashed lines) in FIG. 4D for comparison purposes.

The LINAC 203 has been positioned to the same first position 401 relative to the treatment couch 206. At the first position, there is a distance margin 420 between the treatment couch 206 and the LINAC 203 and robotic arm 402. The distance margin 420 of the robotic treatment delivery system 450 is greater than the distance margin 410 of the conventional robotic treatment delivery system 400. The robotic arm 402, which includes a redundant joint, may position the LINAC 203 to increase the distance margin between the robotic arm and other obstacles in the treatment room. Not only is the distance margin 420 greater than the distance margin 410, but the robotic arm 402 may position the LINAC 203 to the first position 401 through a first path, which has a higher distance margin between an obstacle (treatment couch 206) and the robotic arm 402 than a second path to the same position 401, such as the path taken by the robotic arm 102 to position the LINAC 103.

The robotic arm 402 may position the LINAC 203 to have a TCP or treatment target in multiple locations within the workspace or treatment area. The workspace or treatment area, however, may be limited by positioning restrictions, for example, obstructions caused by a possible collision between either the LINAC 203, the treatment couch 206, or their corresponding robotic arms with components of the system, such as the LINAC 203, treatment couch 206, imaging sources 207, detectors 208, and/or robotic arms 202 and 302 or obstructions of the radiation beam of the LINAC 203 with any of these above mentioned components. For example, the x-ray imaging sources 207 may prevent the LINAC 203 from being positioned where the x-ray imaging sources 207 are mounted because positioning it there would result in a possible collision (e.g., collision obstructions). Similarly, the LINAC 203 may not be positioned under the treatment couch 206 due to the placement of the detectors 208 (e.g., collision obstructions). Another example of a positioning restriction is obstructions of the radiation beam from the LINAC 203 due to other components, for example, the detectors 208 and/or x-ray imaging sources 207 (e.g., beam obstructions). Another obstruction may be caused by the ground. Using the robotic arm having at least one redundant joint, these positioning restrictions may be overcome. By overcoming the positioning restrictions, the workspace may be increased because more nodes for positioning the LINAC 203 may become available, as describe with respect to FIG. 5. In addition to the increase in available nodes in the workspace, the robotic arm having at least one redundant joint may increase the number of available paths to already existing nodes in the workspace. Also, once the LINAC 203 has been positioned to a position, one or more links of the robotic arm may be moved. For example, the one or more links may be moved to increase the distance margin between the robotic arm and an obstacle in the treatment room, such as the treatment couch 206. In addition, using the one or more links having one or more redundant joints, the robotic arm may maneuver the medical tool within a constrained volume without colliding with obstacles outside the constrained volume.

Figure 4D:
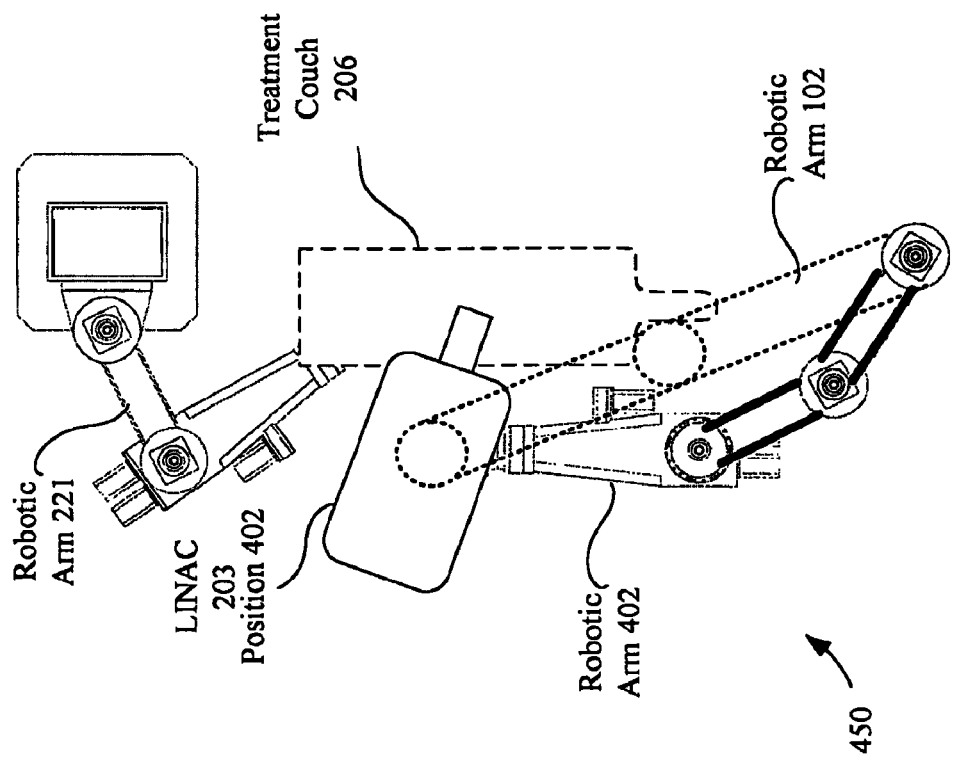
FIG. 4D illustrates a top side view of the robotic treatment delivery system of FIG. 4B in the second position relative to the treatment couch, according to one embodiment.
Figure 4C:
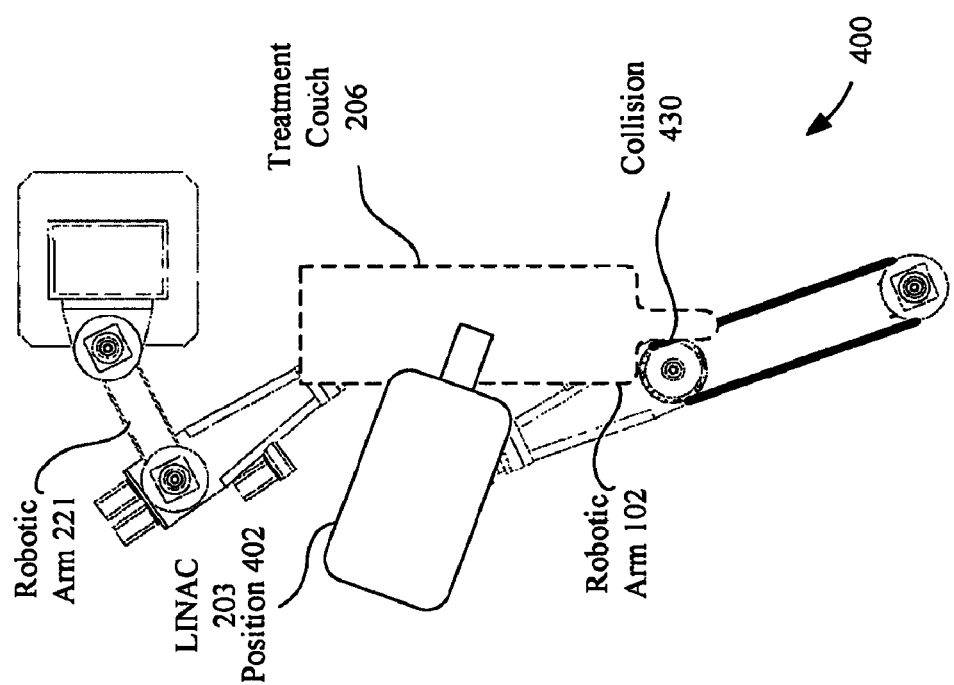
FIG. 4C illustrates a top side view of the conventional robotic treatment delivery system of FIG. 4A in a second position relative to the treatment couch.

FIG. 4C illustrates a top side view of the conventional robotic treatment delivery system 400 of FIG. 4A in a second position 402 relative to the treatment couch 206. If the robotic arm 102 were to position the LINAC 203 to the second position 402, there would be a collision 430 between the robotic arm 102 and the treatment couch 206. As such, the second position 402 is an obstructed location and is unavailable as a possible node in the workspace.

FIG. 4D illustrates a top side view of the robotic treatment delivery system 450 of FIG. 4B in the second position 402 relative to the treatment couch 206, according to one embodiment. Unlike the robotic arm 102, the robotic arm 402 may position the LINAC 203 at the second position 402, which is considered a previously obstructed location caused by a positioning restriction, without a collision between the robotic arm 402 and the treatment couch 206. The robotic arm 102 has been illustrated (dashed lines) in FIG. 4D for comparison purposes.

In another embodiment, movement of the robotic arm 402 and the robotic arm 221 may be dynamically coordinated. The dynamic coordination of movement between the treatment couch 206 and the LINAC 203 may increase a number of treatment targets within a mechanical range of motion of the robotic arm, may create a treatment target in a previously obstructed location caused by a positioning restriction within a mechanical range of motion of the robotic arm 402, or a positioning restriction within a mechanical range of motion of the robotic arm 221. In one embodiment, the previously obstructed location may be caused by an obstruction of a possible collision, for example, between any two of the following: the LINAC 203, treatment couch 206, robotic arm 202, robotic arm 221, x-ray imaging sources 207, detectors 208, and/or other components of the system. Alternatively, the previously obstructed location may be caused by an obstruction of the radiation beam of the LINAC 203 with any of the following: the robotic arm 202, robotic arm 221, x-ray imaging sources 207, detectors 208, and/or other components of the system. In another embodiment, an anti-collision model may be embedded in the controller to ensure that the patient is not positioned in an orientation and/or position that might cause a possible collision between the treatment couch 206 including the patient's body and other moving parts of the system 400.

Using the robotic arm 402, the LINAC 203 may be positioned in symmetrical positions with respect to the treatment couch 206. The capability of positioning the LINAC 203 with respect to the treatment couch 206 in the symmetrical locations may lead to simplified paths for path planning and contact avoidance planning, calculated before treatment delivery, such as calculated by a treatment planning system during treatment planning. The capability of positioning the LINAC 203 with respect to the treatment couch 206 in symmetrical locations may increase the workspace within which the LINAC 203 may be positioned to direct radiation to a target. The access to direct radiation to targets within various locations of the patient may be increased because the number of nodes in the workspace is increased. For example, the nodes on one side of the treatment couch 206 may also be mirrored on the other side of the treatment couch 206.

The total usable surface area may represent the positions or nodes in which the LINAC 203 may be positioned to emit radiation to the treatment target of the patient. The total usable surface area of the robotic treatment delivery system 450, unlike the total usable surface area of the robotic treatment delivery system 400, is not limited by positioning restrictions as described above. Using the robotic arm 402, the positioning restrictions may be reduced or eliminated. Alternatively, using the robotic arm 202 or 302, the positioning restrictions may be reduced or eliminated.

It should be noted that the unreachable area of the robotic treatment delivery system 400 cannot be cured by merely mounting the robotic arm 102 on the opposite side of the treatment couch 206 because the opposite side will then have the unreachable area due to the obstruction of the treatment couch 206 and the robotic arm 102. In other words, merely mounting the robot-based radiosurgery system on another side does not overcome the positioning restriction due to the obstruction causing the unreachable area of the robotic treatment delivery system 400.

Figure 5:
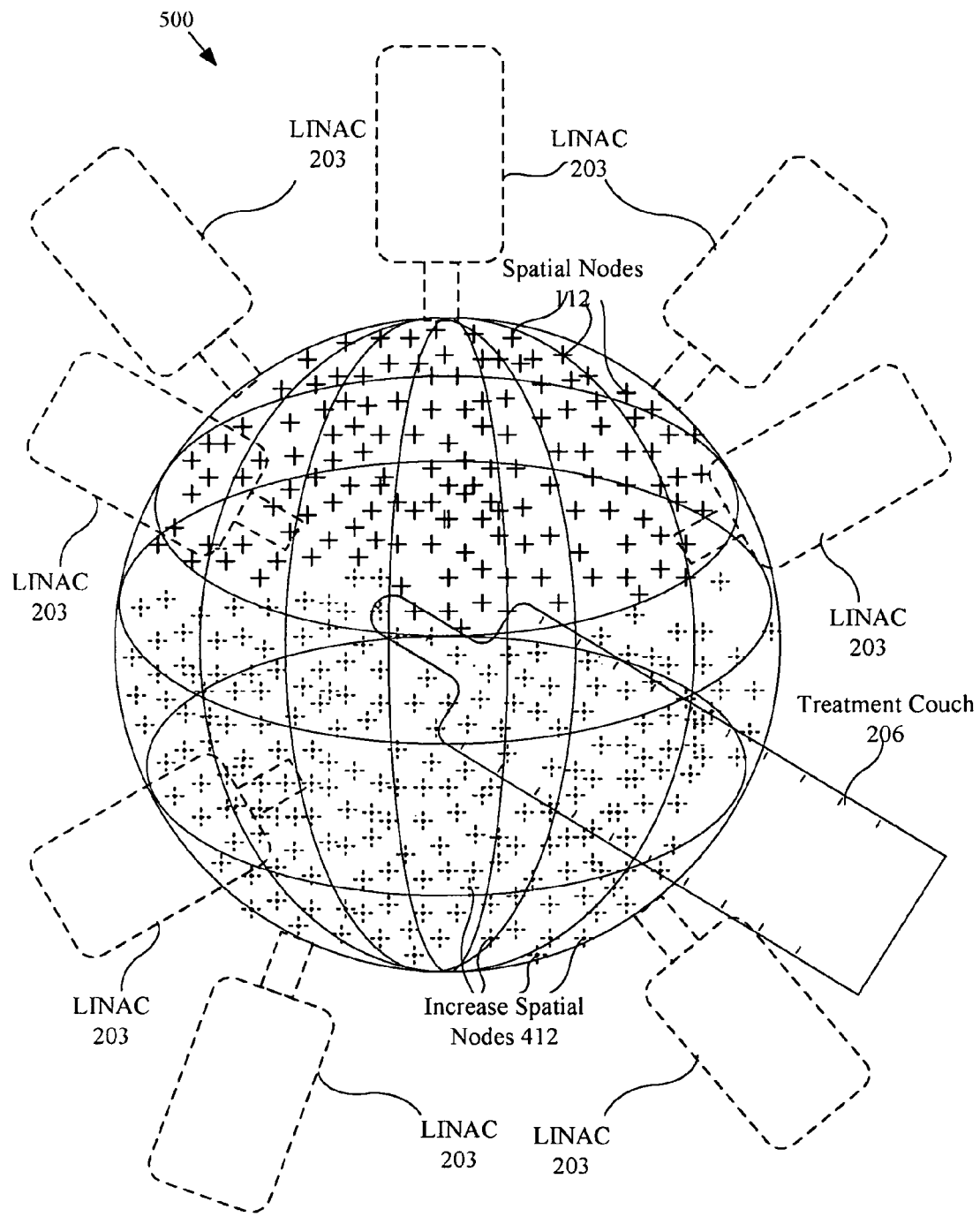
FIG. 5 is a perspective drawing illustrating a workspace of a robotic treatment delivery system, according to one embodiment.

FIG. 5 is a perspective drawing illustrating a workspace 511 of a robotic treatment delivery system 200 or 300, according to one embodiment. As described above, a collection of spatial nodes and associated safe paths interconnecting these spatial nodes is called a "workspace" or "node set". The workspace is representative of the operating envelop of the robotic arm. The workspace 511 includes a set of spatial nodes 511, which reside on the surface of the workspace 511, at which to position the radiation source. Each of the spatial nodes 511 are represented by a "+" symbol (only a couple are labeled). The spatial nodes 511 represent spatial nodes at which the conventional treatment delivery systems can be positioned. A workspace or node set, as described above, is a collection of spatial nodes and associated safe paths interconnecting these spatial nodes. However, unlike the workspace of conventional systems, the workspace 511 and the number of spatial nodes may be increased using the treatment delivery systems 200 or 300. As such, the workspace 511 also includes a set of additional or increased spatial nodes 512, as illustrated as dashed "+". The total number of spatial nodes 511 and increased spatial nodes 512 of the workspace 511 is greater than the total number of spatial nodes 511 of the workspace of a conventional system.

By moving the LINAC 203 using the robotic arm 202 or 302, the LINAC 203 may access certain zones (e.g., spatial nodes) around the treatment couch 206 that were previously blocked or otherwise unreachable in conventional systems. For example, the conventional robotic arm could not position the LINAC 103 around the treatment couch 106 to position the LINAC 103 in certain positions. These blocked positions, however, are not blocked and are reachable for the treatment delivery systems 200 and 300, as described herein. Having greater accessibility to those certain zones, which were previously blocked or otherwise unreachable by the treatment couch in conventional systems, increases the workspace 511 (e.g., spatial nodes at which the LINAC 203 may deliver radiation to the target). Moreover, additional spatial nodes may be accessed that were not accessible by conventional robotic arms because of the distance margin between the conventional robotic arm and the patient.

It should be noted that although workspace 511 is spherical, alternatively, the workspace 511 may have other geometries (e.g., elliptical) and defined for VOIs residing in the head of a patient, or within other areas of a patient. Additionally, multiple workspaces may be defined for different portions of a patient, each having different radius or source axis distances (SADs), such as 650 mm and 800 mm. The SAD is the distance between the collimator in the LINAC 203 and the target within the VOI. The SAD defines the surface area of the workspace. In one embodiment of an elliptical workspace, the SAD may range from 900 mm to 1000 mm. Other SADs may be used.

Spatial nodes 511 and increase spatial nodes 512 reside on the surface of workspace 511. Spatial nodes represent positions where the LINAC 203 is pre-programmed to stop and delivery a dose of radiation to the VOI within the patient. During delivery of a treatment plan, robotic arm 202 moves the LINAC 203 to each and every spatial node 112 and 412, where a dose is determined to be delivered, following a predefined path. The predefine path may also include some spatial nodes 511 and 512 where no dose needs to be delivered, in order to simplify the motions of the robotic arm 202 or 302.

The node set may include spatial nodes that are substantially uniformly distributed over the geometric surface of workspace 511. The node set includes all programmed spatial nodes 511 and 412 and provides a workable number of spatial nodes 511 and 512 for effectively computing treatment plan solutions for most ailments and associated VOIs. The node set provides a reasonably large number of spatial nodes 511 and 512 such that homogeneity and conformality thresholds can be achieved for a large variety of different VOIs, while providing enough vantage points to avoid critical structures within patients. Using the embodiments described herein, the number of spatial nodes is greater than the number of spatial nodes in the conventional systems. It should be appreciated that the node set may include more or less spatial nodes 511 and 512 than is illustrated or discussed. For example, as processing power increases and experience gained creating treatment plans, the average number of spatial nodes 511 and 512 may increase with time to provide greater flexibility and higher quality treatment plans.

During radiation treatment, the patient rests on treatment couch 206, which is maneuvered to position a volume of interest ("VOI") containing a target to a preset position or within an operating range accessible to radiation source of the LINAC 203. The robotic arm 202 or 302 has seven DOF capable of positioning the LINAC 203 with almost an infinite number of positions and orientations within its operating envelope.

As described above, the embodiments described herein have been depicted and described as robotic arms coupled to a LINAC, however, in other embodiments, other robotic manipulators and/or other medical tools may be used. For example, the medical tool may be an imaging source of an imager, a surgical tool, an implantation tool, a treatment couch. In the case of a treatment couch, the robotic arm may position the treatment couch like the LINAC described above to increase a distance margin between the robotic arm and other obstacles in the treatment room, to increase the available workspace, or the like.

The embodiments described herein may allow the LINAC 203 to be positioned at various positioned to direct one or more radiation beams towards a patient on a treatment couch. For example, the LINAC 203 may be positioned to a first position to direct radiation to a target within the head of a patient that is lying on the treatment couch. Alternatively, the LINAC 203 may be positioned to a second position to direct radiation to a target within the patient for a posterior treatment. During posterior treatments, with the patient lying in supine position on the treatment couch, the LINAC 203 may be positioned to be pointed upwards at the patient and deliver the treatment beam from the posterior direction. The LINAC 203 may also be moved to a different location, or in a different orientation at the same location by moving the position and/or orientation at the same location. For example, the robotic arm can position and orient the LINAC 203 above the patient using the substantial vertical, linear DOF (e.g., track 226) and the additional DOF (e.g., redundant-joint, elbow, and shoulder assemblies) to provide the vertical reach, while the wrist assembly 212 provides the orientation of the LINAC 203 with respect to a target in a posterior treatment (e.g., rotate the LINAC 203 about the pitch-axis using the tool-yaw joint of the wrist assembly 212). Alternatively, the LINAC 203 may be positioned and oriented with respect to the target in posterior treatments using other motions of the robotic arm 202. Alternatively, the LINAC 203 at the position 283 is configured to direct radiation to a target in other types of treatments.

FIG. 6 illustrates one embodiment of a method 600 for positioning a medical tool using a robotic manipulator. The method 600 includes providing a medical tool (e.g., LINAC 203) coupled to a robotic manipulator having seven or more DOF, operation 601, and moving the medical tool along seven or more DOF using the robotic manipulator, operation 602.

Moving the medical tool along the seven or more DOF includes moving the medical moving the medical tool in four rotational axes for translational movement of the medical tool along mutually orthogonal x-, y-, and z-coordinate axes, and in three rotational axes for roll-, pitch-, and yaw-rotations of the medical tool about x-, y-, and z-axes, respectively. In one embodiment, the medical tool can be positioned to a fixed position by moving the medical tool using the four rotational axes, and oriented at the fixed position using the three rotational axes. The medical tool may also be moved along a substantially linear DOF. The substantially linear DOF may be in addition to, in place of one of the rotational DOF described above. In on embodiment, the medical tool is moved along a substantially vertical, linear DOF having a substantially linear axis for translational movements of the medical tool along a substantially vertical line in a z-axis that is substantially perpendicular to horizontal coordinate x- and y-axes. In another embodiment, the medical tool is moved along a substantially horizontal, linear DOF having a substantially linear axis for translational movements of the medical tool along a horizontal line in the mutually orthogonal horizontal coordinate x- and y-axes that is substantially perpendicular to the z-axis. The medical tool may be moved along a substantially linear axis throughout substantially an entire range of motion of the medical tool without moving the medical tool in the six (for seven DOF) or seven (for eight DOF) rotational DOF.

In another embodiment, the medical tool can be rotated about the z-axis, y-axis, and y-axis using a tool-yaw joint, a tool-pitch joint, and a tool-roll joint of a robotic manipulator. The medical tool can also be rotated about first, second, and third rotational axes using a redundant joint, an elbow joint, and a first shoulder joint, respectively, of the robotic manipulator. The medical tool can be either rotating about a fourth rotational axis using a second shoulder joint or translated about a substantially linear axis using a track and a track mount assembly for the seventh DOF.

In another embodiment, the medical tool can be positioned to a fixed position using a robotic manipulator, and maintained at the fixed position, while moving the robotic manipulator. The medical tool can be positioned within a constrained volume without colliding with an object outside of the constrained volume.

The method may also include positioning the medical tool to a previously obstructed location caused by a position restriction within a mechanical range of motion of the robotic manipulator and the medical tool. In another embodiment, the medical tool is positioned to a first position to a second position through a first path, instead of through an obstructed path caused by an obstacle to the same second position. In another embodiment, the medical tool is positioned from a first position to a second position through a first path, the first path having a higher distance margin between an obstacle and the robotic manipulator and medical tool than a second path to the same second position.

FIG. 7 illustrates another embodiment of a method for maintaining a medical tool at the fixed position. The method includes positioning a medical tool to a fixed position using a robotic manipulator, operation 701; and maintaining the medical tool at the fixed position, while moving the robotic manipulator, operation 702. In one embodiment, the robotic manipulator includes multiple rigid links interconnected by joints. While the medical tool is maintained at the fixed position, one or more of the rigid links of the robotic manipulator may be moved. The medical tool can be positioned within a constrained volume without colliding with an object outside of the constrained volume.

In another embodiment, the method includes providing an imaging system having an imaging field of view, and maintaining the LINAC 203 substantially outside of the imaging field of view for all supported treatment positions.

In one embodiment, moving the LINAC 203 and the treatment couch 206 may include dynamically coordinating an orientation and position of the LINAC 203 and the treatment couch 206 using the controller. In another embodiment, moving the LINAC 203 and the treatment couch 206 includes aligning a radiation source of the LINAC 203 with a treatment target within a patient disposed on the treatment couch 206. In another embodiment, moving the LINAC 203 and the treatment couch 206 further includes positioning the LINAC 203 and the treatment couch 206 to create a treatment target in a previously obstructed location within a mechanical range of motion of the robotic arm 202 and the LINAC 203.

Figure 8:
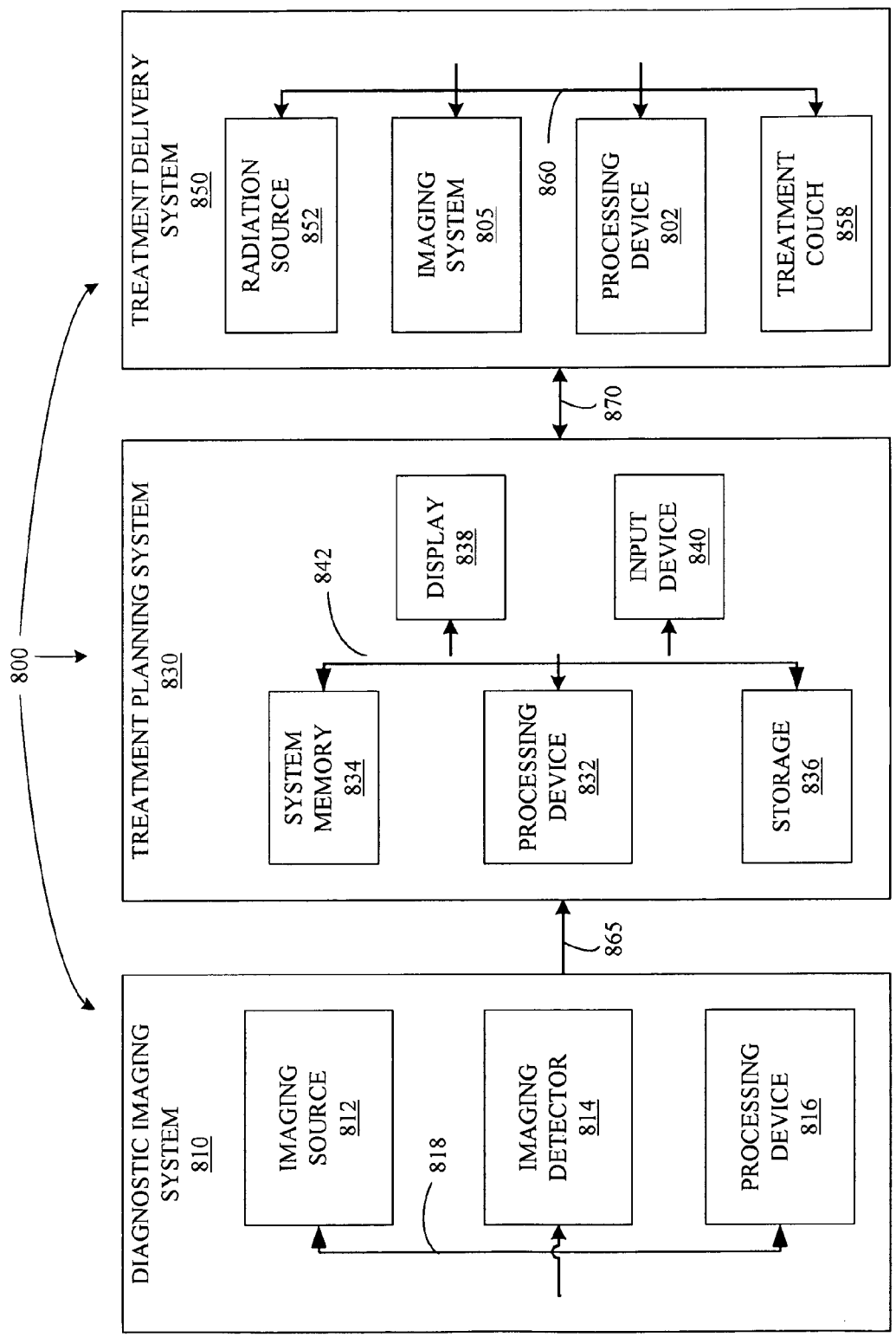
FIG. 8 illustrates a block diagram of one embodiment of a treatment system that may be used to perform radiation treatment in which embodiments of the present invention may be implemented.

FIG. 8 illustrates a block diagram of one embodiment of a treatment system 800 that may be used to perform radiation treatment in which embodiments of the present invention may be implemented. The depicted treatment system 800 includes a diagnostic imaging system 810, a treatment planning system 830, and a treatment delivery system 850. In other embodiments, the treatment system 800 may include fewer or more component systems.

The diagnostic imaging system 810 is representative of any system capable of producing medical diagnostic images of a volume of interest (VOI) in a patient, which images may be used for subsequent medical diagnosis, treatment planning, and/or treatment delivery. For example, the diagnostic imaging system 810 may be a computed tomography (CT) system, a single photon emission computed tomography (SPECT) system, a magnetic resonance imaging (MRI) system, a positron emission tomography (PET) system, a near infrared fluorescence imaging system, an ultrasound system, or another similar imaging system. For ease of discussion, any specific references herein to a particular imaging system such as a CT x-ray imaging system (or another particular system) is representative of the diagnostic imaging system 810, generally, and does not preclude other imaging modalities, unless noted otherwise.

The illustrated diagnostic imaging system 810 includes an imaging source 812, an imaging detector 814, and a processing device 816. The imaging source 812, imaging detector 814, and processing device 816 are coupled to one another via a communication channel 818 such as a bus. In one embodiment, the imaging source 812 generates an imaging beam (e.g., x-rays, ultrasonic waves, radio frequency waves, etc.) and the imaging detector 814 detects and receives the imaging beam. Alternatively, the imaging detector 814 may detect and receive a secondary imaging beam or an emission stimulated by the imaging beam from the imaging source (e.g., in an MRI or PET scan). In one embodiment, the diagnostic imaging system 810 may include two or more diagnostic imaging sources 812 and two or more corresponding imaging detectors 814. For example, two x-ray sources 812 may be disposed around a patient to be imaged, fixed at an angular separation from each other (e.g., 90 degrees, 45 degrees, etc.) and aimed through the patient toward corresponding imaging detectors 814, which may be diametrically opposed to the imaging sources 814. A single large imaging detector 814, or multiple imaging detectors 814, also may be illuminated by each x-ray imaging source 814. Alternatively, other numbers and configurations of imaging sources 812 and imaging detectors 814 may be used.

The imaging source 812 and the imaging detector 814 are coupled to the processing device 816 to control the imaging operations and process image data within the diagnostic imaging system 810. In one embodiment, the processing device 816 may communicate with the imaging source 812 and the imaging detector 814. Embodiments of the processing device 816 may include one or more general-purpose processors (e.g., a microprocessor), special purpose processors such as a digital signal processor (DSP), or other type of devices such as a controller or field programmable gate array (FPGA). The processing device 816 also may include other components (not shown) such as memory, storage devices, network adapters, and the like. In one embodiment, the processing device 816 generates digital diagnostic images in a standard format such as the Digital Imaging and Communications in Medicine (DICOM) format. In other embodiments, the processing device 816 may generate other standard or non-standard digital image formats.

Additionally, the processing device 816 may transmit diagnostic image files such as DICOM files to the treatment planning system 830 over a data link 860. In one embodiment, the data link 860 may be a direct link, a local area network (LAN) link, a wide area network (WAN) link such as the Internet, or another type of data link. Furthermore, the information transferred between the diagnostic imaging system 810 and the treatment planning system 830 may be either pulled or pushed across the data link 860, such as in a remote diagnosis or treatment planning configuration. For example, a user may utilize embodiments of the present invention to remotely diagnose or plan treatments despite the existence of a physical separation between the system user and the patient.

The illustrated treatment planning system 830 includes a processing device 832, a system memory device 834, an electronic data storage device 836, a display device 838, and an input device 840. The processing device 832, system memory 834, storage 836, display 838, and input device 840 may be coupled together by one or more communication channel 842 such as a bus.

The processing device 832 receives and processes image data. The processing device 832 also processes instructions and operations within the treatment planning system 830. In certain embodiments, the processing device 832 may include one or more general-purpose processors (e.g., a microprocessor), special purpose processors such as a digital signal processor (DSP), or other types of devices such as a controller or field programmable gate array (FPGA).

In particular, the processing device 832 may be configured to execute instructions for performing treatment operations discussed herein. For example, the processing device 832 may identify a non-linear path of movement of a target within a patient and develop a non-linear model of the non-linear path of movement. In another embodiment, the processing device 832 may develop the non-linear model based on multiple position points and multiple direction indicators. In another embodiment, the processing device 832 may generate multiple correlation models and select one of the models to derive a position of the target. Furthermore, the processing device 832 may facilitate other diagnosis, planning, and treatment operations related to the operations described herein.

In one embodiment, the system memory 834 may include random access memory (RAM) or other dynamic storage devices. As described above, the system memory 834 may be coupled to the processing device 832 by the communication channel 842. In one embodiment, the system memory 834 stores information and instructions to be executed by the processing device 832. The system memory 834 also may be used for storing temporary variables or other intermediate information during execution of instructions by the processing device 832. In another embodiment, the system memory 834 also may include a read only memory (ROM) or other static storage device for storing static information and instructions for the processing device 832.

In one embodiment, the storage 836 is representative of one or more mass storage devices (e.g., a magnetic disk drive, tape drive, optical disk drive, etc.) to store information and instructions. The storage 836 and/or the system memory 834 also may be referred to as machine readable media. In a specific embodiment, the storage 836 may store instructions to perform the modeling operations discussed herein. For example, the storage 836 may store instructions to acquire and store data points, acquire and store images, identify non-linear paths, develop linear and/or non-linear correlation models, and so forth. In another embodiment, the storage 836 may include one or more databases.

In one embodiment, the display 838 may be a cathode ray tube (CRT) display, a liquid crystal display (LCD), or another type of display device. The display 838 displays information (e.g., a two-dimensional or 3D representation of the VOI) to a user. The input device 840 may include one or more user interface devices such as a keyboard, mouse, trackball, or similar device. The input device(s) 840 may also be used to communicate directional information, to select commands for the processing device 832, to control cursor movements on the display 838, and so forth.

Although one embodiment of the treatment planning system 830 is described herein, the described treatment planning system 830 is only representative of an exemplary treatment planning system 830. Other embodiments of the treatment planning system 830 may have many different configurations and architectures and may include fewer or more components. For example, other embodiments may include multiple buses, such as a peripheral bus or a dedicated cache bus. Furthermore, the treatment planning system 830 also may include Medical Image Review and Import Tool (MIRIT) to support DICOM import so that images can be fused and targets delineated on different systems and then imported into the treatment planning system 830 for planning and dose calculations. In another embodiment, the treatment planning system 830 also may include expanded image fusion capabilities that allow a user to plan treatments and view dose distributions on any one of the various imaging modalities such as MRI, CT, PET, and so forth. Furthermore, the treatment planning system 830 may include one or more features of convention treatment planning systems.

In one embodiment, the treatment planning system 830 may share a database on the storage 836 with the treatment delivery system 850 so that the treatment delivery system 850 may access the database prior to or during treatment delivery. The treatment planning system 830 may be linked to treatment delivery system 850 via a data link 870, which may be a direct link, a LAN link, or a WAN link, as discussed above with respect to data link 860. Where LAN, WAN, or other distributed connections are implemented, any of components of the treatment system 800 may be in decentralized locations so that the individual systems 810, 830 and 850 may be physically remote from one other. Alternatively, some or all of the functional features of the diagnostic imaging system 810, the treatment planning system 830, or the treatment delivery system 850 may be integrated with each other within the treatment system 800.

The illustrated treatment delivery system 850 includes a radiation source 852, an imaging system 854, a processing device 856, and a treatment couch 858. The radiation source 852, imaging system 854, processing device 856, and treatment couch 858 may be coupled to one another via one or more communication channels 860. One example of a treatment delivery system 850 is shown and described in more detail with reference to FIG. 4A.

In one embodiment, the radiation source 852 is a therapeutic or surgical radiation source 852 to administer a prescribed radiation dose to a target volume in conformance with a treatment plan. In one embodiment, the radiation source 852 is the LINAC 203, as described herein. Alternatively, the radiation source 852 may be other types of radiation sources as would be appreciated by those of ordinary skill in the art. For example, the target volume may be an internal organ, a tumor, a region. As described above, reference herein to the target, target volume, target region, target area, or internal target refers to any whole or partial organ, tumor, region, or other delineated volume that is the subject of a treatment plan.

In one embodiment, the imaging system 854 of the treatment delivery system 850 captures intra-treatment images of a patient volume, including the target volume, for registration or correlation with the diagnostic images described above in order to position the patient with respect to the radiation source. Similar to the diagnostic imaging system 810, the imaging system 854 of the treatment delivery system 850 may include one or more sources and one or more detectors.

The treatment delivery system 850 also may include a processing device 856 to control the radiation source 852, the imaging system 854, and a treatment couch 858, which is representative of any patient support device. In one embodiment, the treatment couch 858 is the treatment couch 206 coupled to the robotic arm 202 or 302, as described herein. In another embodiment, the treatment couch 858 is the treatment couch coupled to the robotic arm 106, as described herein. Alternatively, other types of patient support devices can be used. In one embodiment, the radiation source 852 is coupled to a first robotic arm (e.g., robotic arm 202), and the treatment couch 858 is coupled to a second robotic arm (e.g., robotic arm 221). The first and second robotic arms may be coupled to the same controller (e.g., controller) or to separate controllers. In one embodiment, the first and second robotic arms are identical robotic arms. In one embodiment, each of the first and second robotic arms includes four rotational DOF and one substantially linear DOF. In another embodiment, each of the first and second robotic arms includes five rotational DOF and one substantially linear DOF. Alternatively, each of the first and second robotic arms includes six rotational DOF and one substantially linear DOF. Alternatively, the first and second robotic arms may include dissimilar number and types of DOF. In another embodiment, the first and second robotic arms are dissimilar types of robotic arms. Alternatively, only the first robotic arm is used to move the LINAC 203 with respect to the treatment couch 206.

The processing device 856 may include one or more general-purpose processors (e.g., a microprocessor), special purpose processors such as a digital signal processor (DSP), or other devices such as a controller or field programmable gate array (FPGA). Additionally, the processing device 856 may include other components (not shown) such as memory, storage devices, network adapters, and the like.

The illustrated treatment delivery system 850 also includes a user interface 862 and a measurement device 864. In one embodiment, the user interface 862 is the user interface 500. In another embodiment, the user interface 862 is the graphical user interface 600. In one embodiment, the user interface 862 allows a user to interface with the treatment delivery system 850. In particular, the user interface 862 may include input and output devices such as a keyboard, a display screen, and so forth. The measurement device 864 may be one or more devices that measure external factors such as the external factors described above, which may influence the radiation that is actually delivered to the target region 20. Some exemplary measurement devices include a thermometer to measure ambient temperature, a hygrometer to measure humidity, a barometer to measure air pressure, or any other type of measurement device to measure an external factor.

In the foregoing specification, embodiments of the invention have been described with reference to specific exemplary embodiments thereof. It will, however, be evident that various modifications and changes may be made thereto without departing from the broader spirit and scope of the present embodiments as set forth in the claims. The specification and drawings are, accordingly, to be regarded in an illustrative rather than a restrictive sense.

What is claimed is:

1. An apparatus, comprising:
    a medical tool; and
    a robotic manipulator coupled to the medical tool to move the medical tool along seven or more degrees of freedom (DOF), wherein the seven or more DOF comprises at least one redundant DOF, wherein the robotic manipulator comprises a plurality of rigid links interconnected by joints allowing either rotational motion or translational displacement, and wherein at least one of the joints is a redundant joint that moves the robotic manipulator in the at least one redundant DOF, wherein the robotic manipulator is a robotic arm, and wherein the robotic manipulator comprises:
        a wrist assembly coupled to the medical tool to move the medical tool in three DOF; and
        an arm assembly coupled to the wrist assembly to move the medical tool in four DOF, wherein the four DOF comprise the at least one redundant DOF.

2. The apparatus of claim 1, wherein the wrist assembly comprises:
    a tool-yaw joint coupled to a mounting plate that supports the medical tool to rotate the medical tool along a first rotational axis;
    a tool-pitch joint coupled to the tool-yaw joint to rotate the medical tool along a second rotational axis; and
    a tool-roll joint coupled to the tool-pitch joint to rotate the medical tool along a third rotational axis.

3. The apparatus of claim 2, wherein the arm assembly comprises:
    an elbow assembly;
    a redundant-joint assembly coupled between the wrist assembly and the elbow assembly;
    a first shoulder assembly coupled to the elbow assembly; and
    a second shoulder assembly coupled to the first shoulder assembly.

4. The apparatus of claim 3, further comprising:
    a redundant joint coupled to the redundant-joint assembly and the elbow assembly, wherein the redundant joint comprises a gearbox to drive rotational movement of the robotic arm in a fourth rotational axis of the robotic arm;
    an elbow joint coupled to the elbow assembly and the first shoulder assembly, wherein the elbow joint comprises an elbow gearbox to drive rotational movement of the robotic arm in a fifth rotational axis of the robotic arm;
    a first shoulder joint coupled to the first shoulder assembly and the second shoulder assembly, wherein the first shoulder joint comprises a first shoulder gearbox to drive rotational movement of the robotic arm in a sixth rotational axis of the robotic arm; and
    a second shoulder joint coupled to the second shoulder assembly and a mount assembly, wherein the second shoulder joint comprises a second shoulder gearbox to drive rotational movement of the robotic arm in a seventh rotational axis of the robotic arm.

5. The apparatus of claim 4, further comprising:
    a track mount assembly coupled to the second shoulder assembly of the robotic arm; and a track coupled to the track mount assembly, wherein the track is configured to move the track mount assembly along an eighth translational axis of the robotic arm.

6. The apparatus of claim 2, wherein the arm assembly comprises:
an elbow assembly coupled to the wrist assembly;
a first shoulder assembly coupled to the elbow assembly;
a second shoulder assembly coupled to the first shoulder assembly,
an elbow joint coupled to the elbow assembly and the first shoulder assembly, wherein the elbow joint comprises an elbow gearbox to drive rotational movement of the robotic arm in a fourth rotational axis of the robotic arm;
a first shoulder joint coupled to the first shoulder assembly and the second shoulder assembly, wherein the first shoulder joint comprises a first shoulder gearbox to drive rotational movement of the robotic arm in a fifth rotational axis of the robotic arm;
a second shoulder joint coupled to the second shoulder assembly and a mount assembly, wherein the second shoulder joint comprises a second shoulder gearbox to drive rotational movement of the robotic arm in a sixth rotational axis of the robotic arm; and
a redundant joint coupled to the first and second shoulder assemblies, wherein the redundant joint comprises a third shoulder gearbox to drive rotational movement of the robotic arm in a seventh rotational axis of the robotic arm.

7. The apparatus of claim 2, wherein the arm assembly comprises:
an elbow assembly coupled to the wrist assembly;
a first shoulder assembly coupled to the elbow assembly;
a redundant-joint assembly coupled between the elbow assembly and the first shoulder assembly; and
a second shoulder assembly coupled to the first shoulder assembly.

8. The apparatus of claim 7, further comprising:
an elbow joint coupled to the wrist assembly and the elbow assembly, wherein the elbow joint comprises an elbow gearbox to drive rotational movement of the robotic arm in a fourth rotational axis of the robotic arm;
a redundant joint coupled to the elbow assembly and the first shoulder assembly, wherein the redundant joint comprises a gearbox to drive rotational movement of the robotic arm in a fifth rotational axis of the robotic arm;
a first shoulder joint coupled to the first shoulder assembly and the second shoulder assembly, wherein the first shoulder joint comprises a first shoulder gearbox to drive rotational movement of the robotic arm in a sixth rotational axis of the robotic arm; and
a second shoulder joint coupled to the second shoulder assembly and a mount assembly, wherein the second shoulder joint comprises a second shoulder gearbox to drive rotational movement of the robotic arm in a seventh rotational axis of the robotic arm.

9. The apparatus of claim 1, wherein seven DOF of the seven or more DOF comprise:
four rotational axes for translational movement of the medical tool along mutually orthogonal x-, y-, and z-coordinate axes; and
three rotational axes for roll-, pitch-, and yaw- rotations of the medical tool about x-, y-, and z- axes, respectively.

10. The apparatus of claim 9, further comprises an eighth DOF, wherein the eighth DOF is a substantially linear DOF that includes a substantially linear axis for translational movement of the medical tool along the substantially linear axis.

11. The apparatus of claim 10, wherein the substantially linear DOF is a first DOF of the eight DOF, wherein the first DOF is configured to move the other seven rotational DOF of the robotic manipulator, and wherein the first DOF is the DOF closest to the base end of the robotic arm.

12. The apparatus of claim 1, wherein seven DOF of the seven or move DOF comprises:
comprise:
three rotational axes for translational movement of the medical tool along mutually orthogonal x-, y-, and z-coordinate axes;
three rotational axes for roll-, pitch-, and yaw- rotations of the medical tool about x-, y-, and z- axes, respectively; and
a translational axis for translational movement of the medical tool along a substantially linear axis.

13. The apparatus of claim 1, wherein the medical tool is a linear accelerator (LINAC).

14. The apparatus of claim 13, wherein by moving the medical tool along the seven or more DOF, including the at least one redundant DOF, the robotic manipulator increases a workspace of the LINAC, and wherein the workspace comprises a number of nodes at which the LINAC can be positioned to deliver radiation to a target.

15. The apparatus of claim 1, wherein the medical tool is an imaging source of an imager.

16. The apparatus of claim 1, wherein the medical tool is a surgical tool.

17. The apparatus of claim 1, wherein the medical tool is an implantation tool.

18. The apparatus of claim 1, wherein the medical tool is a treatment couch.

19. The apparatus of claim 1, further comprising a controller coupled to the robotic manipulator to move the robotic manipulator and the medical tool in the seven or more DOF.

20. A method, comprising:
providing a medical tool coupled to a robotic manipulator having seven or more degrees of freedom (DOF), wherein the seven DOF comprise at least one redundant DOF, wherein the robotic manipulator comprises a plurality of rigid links of the robotic manipulator, the plurality of rigid links being interconnected by joints that allow either rotational motion or translational displacement, wherein at least one of the joints is a redundant joint that moves the robotic manipulator in the at least one redundant DOF, wherein the robotic manipulator comprises a wrist assembly coupled to the medical tool and an arm assembly coupled to the wrist assembly; and
moving the medical tool using the robotic manipulator along seven or more degrees of freedom (DOF), wherein the moving the medical tool comprises:
moving the medical tool in three DOF using the wrist assembly; and
moving the medical tool in four DOF using the arm assembly, wherein the four DOF comprise the at least one redundant DOF.

21. The method of claim 20, wherein moving the medical tool along the seven or more DOF comprises:
moving the medical tool in four rotational axes for translational movement of the medical tool along mutually orthogonal x-, y-, and z- coordinate axes; and
moving the medical tool in three rotational axes for roll-, pitch-, and yaw-rotations of the medical tool about x-, y-, and z- axes, respectively.

22. The method of claim 21, further comprising:
positioning the medical tool to a fixed position by moving the medical tool using the four rotational axes; and orienting the medical tool at the fixed position by moving the medical tool using the three rotational axes.

23. The method of claim 21, further comprising:
positioning the medical tool to a fixed position using the robotic manipulator; and
maintaining the medical tool at the fixed position, while moving the robotic manipulator.

24. The method of claim 21, further comprising positioning the medical tool to a previously obstructed location caused by a position restriction within a mechanical range of motion of the robotic manipulator and the medical tool.

25. The method of claim 21, further comprising positioning the medical tool from a first position to a second position through a first path, instead of through an obstructed path caused by an obstacle to the same second position.

26. The method of claim 21, further comprising positioning the medical tool from a first position to a second position through a first path, wherein the first path has a higher distance margin between an obstacle and the robotic manipulator and medical tool than a second path to the same second position.

27. The method of claim 21, further comprising positioning the medical tool within a constrained volume without colliding with an object outside the constrained volume.

28. The method of claim 21, further comprising moving the medical tool along a substantially linear DOF.

29. A method, comprising:
positioning a medical tool to a fixed position using a robotic manipulator comprising seven or more degrees of freedom (DOF), wherein the seven DOF comprise at least one redundant DOF, wherein the robotic manipulator comprises a plurality of rigid links of the robotic manipulator, the plurality of rigid links being interconnected by joints that allow either rotational motion or translational displacement, wherein at least one of the joints is a redundant joint that moves the robotic manipulator in the at least one redundant DOF, wherein the robotic manipulator comprises a wrist assembly coupled to the medical tool and an arm assembly coupled to the wrist assembly, wherein the positioning comprises:
moving the medical tool in three DOF using the wrist assembly; and
moving the medical tool in four DOF using the arm assembly, wherein the four DOF comprise the at least one redundant DOF; and
maintaining the medical tool at the fixed position, while moving the robotic manipulator, and wherein the maintaining the medial tool at the fixed position comprises moving one or more of the plurality of rigid links of the robotic manipulator, while maintaining the medical tool at the fixed position.

30. A system apparatus, comprising:
a linear accelerator (LINAC);
a robotic manipulator coupled to the LINAC, the robotic manipulator configured to move the LINAC in at least seven degrees of freedom (DOF), wherein the at least seven DOF comprises at least one redundant DOF, wherein the robotic manipulator comprises a plurality of rigid links interconnected by joints allowing either rotational motion or translational displacement, and wherein at least one of the joints is a redundant joint that moves the robotic manipulator in the at least one redundant DOF, wherein the robotic manipulator is a robotic arm, and wherein the robotic manipulator comprises:
a wrist assembly coupled to the LINAC to move the LINAC in three DOF; and
an arm assembly coupled to the wrist assembly to move the LINAC in four DOF, wherein the four DOF comprise the at least one redundant DOF;
a controller coupled to the robotic manipulator to control movement of the LINAC to align a radiation source of the LINAC with a treatment target; and
an imaging system to generate a plurality of images of the treatment target.

31. The system of claim 30, wherein the controller is configured to position the LINAC to access a treatment target in a previously obstructed location caused by a position restriction within a mechanical range of motion of the robotic manipulator and the LINAC.

32. The system of claim 30, wherein the imaging system comprises:
a pair of x-ray sources; and
a pair of x-ray image detectors, wherein each image detector is disposed opposite a respective source.

* * * * *